(12) United States Patent
Truckai et al.

(10) Patent No.: US 10,172,659 B2
(45) Date of Patent: *Jan. 8, 2019

(54) BONE TREATMENT SYSTEMS AND METHODS

(71) Applicant: DFINE, Inc., South Jordan, UT (US)

(72) Inventors: Csaba Truckai, Saratoga, CA (US); John H. Shadduck, Menlo Park, CA (US)

(73) Assignee: DFINE, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/477,678

(22) Filed: Apr. 3, 2017

(65) Prior Publication Data

US 2017/0333103 A1 Nov. 23, 2017

Related U.S. Application Data

(63) Continuation of application No. 14/683,506, filed on Apr. 10, 2015, now Pat. No. 9,610,110, which is a (Continued)

(51) Int. Cl.
*A61B 17/88* (2006.01)
*A61B 17/00* (2006.01)
(Continued)

(52) U.S. Cl.
CPC ...... *A61B 17/8805* (2013.01); *A61B 17/8822* (2013.01); *A61B 17/8827* (2013.01);
(Continued)

(58) Field of Classification Search
CPC .................................................. A61B 17/8833
See application file for complete search history.

(56) References Cited

U.S. PATENT DOCUMENTS 3,349,840 A 10/1967 Tope et al.
4,250,887 A 2/1981 Dardik et al.
(Continued)

FOREIGN PATENT DOCUMENTS

EP 0361408 4/1990
EP 0581387 2/1994
(Continued)

OTHER PUBLICATIONS

European Examination Report dated Feb. 6, 2013 for EP05848386.8.

(Continued)

*Primary Examiner* — Eduardo C Robert
*Assistant Examiner* — Tara R Carter
(74) *Attorney, Agent, or Firm* — Stoel Rives LLP

(57) ABSTRACT

The present invention relates in certain embodiments to medical devices for treating vertebral compression fractures. More particularly, embodiments of the invention relate to instruments and methods for controllably restoring vertebral body height by controlling the flow of bone cement into the interior of a vertebra and the application of forces causes by the cement flow. An exemplary system utilizes Rf energy in combination a conductive bone cement for selectively polymerizing the inflow plume to increase the viscosity of the cement. In one aspect of the invention, the system utilizes a controller to control bone cement flow parameters to either allow or disallow cement interdigitation into cancellous bone. A method of the invention includes pulsing the flows of bone cement wherein high acceleration of the flow pulses can apply expansion forces across the surface of the cement plume to reduce a vertebral fracture.

20 Claims, 21 Drawing Sheets

Related U.S. Application Data continuation of application No. 13/734,829, filed on Jan. 4, 2013, now Pat. No. 9,005,210, which is a continuation of application No. 12/786,362, filed on May 24, 2010, now Pat. No. 8,348,955, which is a continuation of application No. 11/209,035, filed on Aug. 22, 2005, now Pat. No. 7,722,620, which is a continuation-in-part of application No. 11/208,448, filed on Aug. 20, 2005, now Pat. No. 7,717,918, which is a continuation-in-part of application No. 11/196,045, filed on Aug. 2, 2005, now Pat. No. 8,070,753, which is a continuation-in-part of application No. 11/165,652, filed on Jun. 24, 2005, now Pat. No. 7,559,932.

(60) Provisional application No. 60/633,509, filed on Dec. 6, 2004.

(51) Int. Cl.
  *A61F 2/44* (2006.01)
  *A61B 17/70* (2006.01)
  *A61B 17/56* (2006.01)

(52) U.S. Cl.
  CPC .......... *A61B 17/8836* (2013.01); *A61B 17/70* (2013.01); *A61B 2017/00022* (2013.01); *A61B 2017/00026* (2013.01); *A61B 2017/00084* (2013.01); *A61B 2017/564* (2013.01); *A61F 2/44* (2013.01)

(56) References Cited

U.S. PATENT DOCUMENTS

| | | |
|---|---|---|
| 4,265,618 A | 5/1981 | Herskovitz et al. |
| 4,280,233 A | 7/1981 | Raab |
| 4,294,251 A | 10/1981 | Grennwald et al. |
| 4,338,925 A | 7/1982 | Miller |
| 4,377,168 A | 3/1983 | Rzasa et al. |
| 4,386,603 A | 6/1983 | Mayfield |
| 4,433,677 A | 2/1984 | Ulrich et al. |
| 4,573,454 A | 3/1986 | Hoffman |
| 4,611,582 A | 9/1986 | Duff |
| 4,653,489 A | 3/1987 | Tronzo |
| 4,735,625 A | 4/1988 | Davidson |
| 4,772,287 A | 9/1988 | Ray et al. |
| 4,773,402 A | 9/1988 | Asher et al. |
| 4,849,223 A | 7/1989 | Pratt et al. |
| 4,959,104 A | 9/1990 | Iino et al. |
| 4,963,151 A | 10/1990 | Ducheyene et al. |
| 4,969,888 A | 11/1990 | Scholten et al. |
| 4,969,906 A | 11/1990 | Kronman |
| 5,030,220 A | 7/1991 | Howland |
| 5,037,437 A | 8/1991 | Matsen, III |
| 5,051,482 A | 9/1991 | Tepic |
| 5,108,404 A | 4/1992 | Scholten et al. |
| 5,130,950 A | 7/1992 | Orban et al. |
| 5,145,250 A | 9/1992 | Planck et al. |
| 5,306,275 A | 4/1994 | Bryan |
| 5,431,654 A | 7/1995 | Nic |
| 5,514,135 A | 5/1996 | Earle |
| 5,542,928 A | 8/1996 | Evans et al. |
| 5,574,075 A | 11/1996 | Draemert |
| 5,593,407 A | 1/1997 | Reis |
| 5,679,299 A | 10/1997 | Gilbert et al. |
| 5,693,099 A | 12/1997 | Harle |
| 5,788,711 A | 8/1998 | Lehner et al. |
| 5,810,815 A | 9/1998 | Morales |
| 5,814,681 A | 9/1998 | Hino et al. |
| 5,827,289 A | 10/1998 | Reiley et al. |
| 5,954,716 A | 9/1999 | Sharkey et al. |
| 5,972,015 A | 10/1999 | Scribner et al. |
| 6,019,760 A | 2/2000 | Metz-Stavenhagen et al. |
| 6,048,346 A | 4/2000 | Reiley et al. |
| 6,075,067 A | 6/2000 | Lidgren |
| 6,122,549 A | 9/2000 | Sharkey et al. |
| 6,171,312 B1 | 1/2001 | Beaty |
| 6,214,012 B1 | 4/2001 | Karpman et al. |
| 6,231,615 B1 | 5/2001 | Preissman |
| 6,235,043 B1 | 5/2001 | Reiley et al. |
| 6,236,020 B1 | 5/2001 | Friedman |
| 6,241,734 B1 | 6/2001 | Scribner et al. |
| 6,248,110 B1 | 6/2001 | Reiley et al. |
| 6,261,289 B1 | 7/2001 | Levy |
| 6,264,659 B1 | 7/2001 | Ross et al. |
| 6,280,456 B1 | 8/2001 | Scribner et al. |
| 6,309,420 B1 | 10/2001 | Preissman |
| 6,312,254 B1 | 11/2001 | Friedman |
| 6,316,885 B1 | 11/2001 | Collins et al. |
| 6,319,255 B1 | 11/2001 | Grundei et al. |
| 6,332,894 B1 | 12/2001 | Stalcup et al. |
| 6,358,254 B1 | 3/2002 | Anderson |
| 6,364,883 B1 | 4/2002 | Santilli |
| 6,375,659 B1 | 4/2002 | Erbe et al. |
| 6,395,007 B1 | 5/2002 | Bhatnagar et al. |
| 6,425,923 B1 | 7/2002 | Stalcup et al. |
| 6,436,143 B1 | 8/2002 | Ross et al. |
| 6,439,439 B1 | 8/2002 | Rickard et al. |
| 6,440,169 B1 | 8/2002 | Elberg et al. |
| 6,443,988 B2 | 9/2002 | Felt et al. |
| 6,447,514 B1 | 9/2002 | Stalcup et al. |
| 6,458,127 B1 | 10/2002 | Truckai et al. |
| 6,458,375 B1 | 10/2002 | Gertzman et al. |
| 6,458,812 B1 | 10/2002 | McKittrick et al. |
| 6,485,436 B1 | 11/2002 | Truckai et al. |
| 6,524,102 B2 | 2/2003 | Davis |
| 6,554,830 B1 | 4/2003 | Chappius |
| 6,558,428 B2 | 5/2003 | Park |
| 6,565,572 B2 | 5/2003 | Chappius |
| 6,582,446 B1 | 6/2003 | Marchosky |
| 6,610,079 B1 | 8/2003 | Li et al. |
| 6,613,054 B2 | 9/2003 | Scribner et al. |
| 6,620,185 B1 | 9/2003 | Harvie et al. |
| 6,622,731 B2 | 9/2003 | Daniel et al. |
| 6,632,235 B2 | 10/2003 | Weikel et al. |
| 6,676,664 B1 | 1/2004 | Al-Assir |
| 6,683,280 B1 | 1/2004 | Wofford et al. |
| 6,706,069 B2 | 3/2004 | Berger |
| 6,709,149 B1 | 3/2004 | Tepic et al. |
| 6,712,852 B1 | 3/2004 | Chung et al. |
| 6,719,773 B1 | 4/2004 | Boucher et al. |
| 6,723,095 B2 | 4/2004 | Hammerslag |
| 6,726,691 B2 | 4/2004 | Osorio et al. |
| 6,736,537 B2 | 5/2004 | Coffeen et al. |
| 6,740,093 B2 | 5/2004 | Hochschuler et al. |
| 6,753,358 B2 | 6/2004 | Fischer et al. |
| 6,767,936 B2 | 7/2004 | Walz et al. |
| 6,783,515 B1 | 8/2004 | Miller et al. |
| 6,814,736 B2 | 11/2004 | Reiley et al. |
| 6,832,988 B2 | 12/2004 | Sproul |
| 6,872,403 B2 | 3/2005 | Pienkowski et al. |
| 6,899,713 B2 | 5/2005 | Shaolian et al. |
| 6,929,640 B1 | 8/2005 | Underwood et al. |
| 6,958,061 B2 | 10/2005 | Truckai et al. |
| 6,964,667 B2 | 11/2005 | Shaolian et al. |
| 6,979,341 B2 | 12/2005 | Scribner et al. |
| 6,979,352 B2 | 12/2005 | Reynolds |
| 6,981,981 B2 | 1/2006 | Reiley et al. |
| 6,985,061 B2 | 1/2006 | Hafskjold et al. |
| 6,989,011 B2 | 1/2006 | Paul et al. |
| 7,008,433 B2 | 3/2006 | Voellmicke et al. |
| 7,029,472 B1 | 4/2006 | Fortin |
| 7,044,954 B2 | 5/2006 | Reiley et al. |
| 7,066,938 B2 | 6/2006 | Slivka et al. |
| 7,081,125 B2 | 7/2006 | Edwards et al. |
| 7,108,696 B2 | 9/2006 | Daniel et al. |
| 7,112,201 B2 | 9/2006 | Truckai et al. |
| 7,112,205 B2 | 9/2006 | Carrison |
| 7,115,163 B2 | 10/2006 | Zimmermann |
| 7,153,306 B2 | 12/2006 | Ralph et al. |
| 7,153,307 B2 | 12/2006 | Scribner et al. |
| 7,156,861 B2 | 1/2007 | Scribner et al. |
| 7,160,020 B2 | 1/2007 | Sand |

(56) References Cited

U.S. PATENT DOCUMENTS

| | | |
|---|---|---|
| 7,166,121 B2 | 1/2007 | Reiley et al. |
| 7,191,285 B2 | 3/2007 | Scales et al. |
| 7,226,481 B2 | 6/2007 | Kuslich et al. |
| 7,241,303 B2 | 7/2007 | Reiss et al. |
| 7,250,055 B1 | 7/2007 | Vanderwalle |
| 7,252,672 B2 | 8/2007 | Yetkinler et al. |
| 7,273,523 B2 | 9/2007 | Wenz |
| 7,261,720 B2 | 12/2007 | Stevens et al. |
| 7,306,598 B2 | 12/2007 | Truckai et al. |
| 7,335,200 B2 | 2/2008 | Carli |
| 7,335,203 B2 | 2/2008 | Winslow et al. |
| 7,431,763 B2 | 10/2008 | Zimmerman |
| 7,510,579 B2 | 3/2009 | Preissman |
| 7,559,932 B2 | 7/2009 | Truckai et al. |
| 7,662,133 B2 | 2/2010 | Scarbrorough et al. |
| 7,678,116 B2 | 3/2010 | Truckai et al. |
| 7,682,378 B2 | 3/2010 | Truckai et al. |
| 7,708,733 B2 | 5/2010 | Sanders et al. |
| 7,717,918 B2 | 5/2010 | Truckai et al. |
| 7,717,947 B1 | 5/2010 | Wilberg et al. |
| 7,722,620 B2 | 5/2010 | Truckai et al. |
| 7,722,624 B2 | 5/2010 | Boucher et al. |
| 8,066,712 B2 | 11/2011 | Truckai et al. |
| 8,070,753 B2 * | 12/2011 | Truckai .............. A61B 17/7095 606/94 |
| 8,192,442 B2 | 6/2012 | Truckai et al. |
| 2001/0011190 A1 | 8/2001 | Park |
| 2001/0012968 A1 | 8/2001 | Preissman |
| 2002/0001620 A1 | 1/2002 | Pienkowski et al. |
| 2002/0026195 A1 | 2/2002 | Layne et al. |
| 2002/0068974 A1 | 6/2002 | Kuslich et al. |
| 2002/0082608 A1 | 6/2002 | Reiley et al. |
| 2002/0099385 A1 | 7/2002 | Ralph et al. |
| 2002/0147497 A1 | 10/2002 | Belef et al. |
| 2002/0156483 A1 | 10/2002 | Voellmicke et al. |
| 2002/0161373 A1 | 10/2002 | Osorio et al. |
| 2002/0165582 A1 | 11/2002 | Porter |
| 2003/0012080 A1 | 1/2003 | Coffeen et al. |
| 2003/0220648 A1 | 1/2003 | Osorio et al. |
| 2003/0032733 A1 | 2/2003 | Fisher et al. |
| 2003/0032929 A1 | 2/2003 | McGuckin |
| 2003/0083662 A1 | 5/2003 | Middleton |
| 2003/0130373 A1 | 7/2003 | Walz et al. |
| 2003/0130738 A1 | 7/2003 | Hovda et al. |
| 2003/0171748 A1 | 9/2003 | Truckai et al. |
| 2003/0208192 A1 | 11/2003 | Truckai et al. |
| 2003/0233096 A1 | 12/2003 | Osorio et al. |
| 2004/0006347 A1 | 1/2004 | Sproul |
| 2004/0024410 A1 | 2/2004 | Olson et al. |
| 2004/0059328 A1 | 3/2004 | Daniel et al. |
| 2004/0073308 A1 | 4/2004 | Kuslich et al. |
| 2004/0083002 A1 | 4/2004 | Belef et al. |
| 2004/0092948 A1 | 5/2004 | Stevens et al. |
| 2004/0102845 A1 | 5/2004 | Reynolds |
| 2004/0110285 A1 | 6/2004 | Lendlein et al. |
| 2004/0111088 A1 | 6/2004 | Picetti |
| 2004/0138748 A1 | 7/2004 | Boyer, II et al. |
| 2004/0158247 A1 | 8/2004 | Sitiso et al. |
| 2004/0167561 A1 | 8/2004 | Boucher et al. |
| 2004/0172132 A1 | 9/2004 | Ginn |
| 2004/0186576 A1 | 9/2004 | Biscup et al. |
| 2004/0193171 A1 | 9/2004 | Dimauro et al. |
| 2004/0225296 A1 | 11/2004 | Reiss et al. |
| 2004/0225926 A1 | 11/2004 | Scales et al. |
| 2004/0228898 A1 | 11/2004 | Ross et al. |
| 2004/0267271 A9 | 12/2004 | Scribner et al. |
| 2004/0267272 A1 | 12/2004 | Henniges et al. |
| 2005/0010231 A1 | 1/2005 | Myers |
| 2005/0015148 A1 | 1/2005 | Jansen et al. |
| 2005/0055026 A1 | 3/2005 | Biderman et al. |
| 2005/0059979 A1 | 3/2005 | Yetkinler et al. |
| 2005/0113843 A1 | 5/2005 | Arramon |
| 2005/0119650 A1 | 6/2005 | Sanders et al. |
| 2005/0180806 A1 | 8/2005 | Green et al. |
| 2005/0209595 A1 | 9/2005 | Karmon |
| 2005/0222681 A1 | 10/2005 | Richley et al. |
| 2005/0245938 A1 | 11/2005 | Kochan |
| 2005/0251149 A1 | 11/2005 | Wens |
| 2006/0052743 A1 | 3/2006 | Reynolds |
| 2006/0074433 A1 | 4/2006 | McGill et al. |
| 2006/0079905 A1 | 4/2006 | Beyar et al. |
| 2006/0084979 A1 | 4/2006 | Jackson |
| 2006/0052794 A1 | 5/2006 | McGill et al. |
| 2006/0095138 A1 | 5/2006 | Truckai et al. |
| 2006/0100635 A1 | 5/2006 | Reiley et al. |
| 2006/0122614 A1 | 6/2006 | Truckai et al. |
| 2006/0122621 A1 | 6/2006 | Truckai et al. |
| 2006/0122622 A1 | 6/2006 | Truckai et al. |
| 2006/0122623 A1 | 6/2006 | Truckai et al. |
| 2006/0122624 A1 | 6/2006 | Truckai et al. |
| 2006/0122625 A1 | 6/2006 | Truckai et al. |
| 2006/0150862 A1 | 7/2006 | Zhao et al. |
| 2006/0264967 A1 | 11/2006 | Ferreyro et al. |
| 2007/0022912 A1 | 2/2007 | Zimmermann |
| 2007/0027230 A1 | 2/2007 | Beyer et al. |
| 2007/0112299 A1 | 5/2007 | Smit et al. |
| 2007/0118144 A1 | 5/2007 | Truckai et al. |
| 2007/0162043 A1 | 7/2007 | Truckai et al. |
| 2007/0185231 A1 | 8/2007 | Liu et al. |
| 2007/0191858 A1 | 8/2007 | Truckai et al. |
| 2007/0191964 A1 | 8/2007 | Preissman |
| 2007/0233077 A1 | 10/2007 | Khalili |
| 2007/0233089 A1 | 10/2007 | Dipoto et al. |
| 2007/0233148 A1 | 10/2007 | Truckai et al. |
| 2007/0288014 A1 | 12/2007 | Shadduck et al. |
| 2007/0299445 A1 | 12/2007 | Shadduck et al. |
| 2007/0299450 A1 | 12/2007 | Her et al. |
| 2008/0021465 A1 | 1/2008 | Shadduck et al. |
| 2008/0021466 A1 | 1/2008 | Shadduck et al. |
| 2008/0058818 A1 | 3/2008 | Schwab |
| 2008/0103505 A1 | 5/2008 | Fransen |
| 2008/0132956 A1 | 6/2008 | Biedernamm et al. |
| 2008/0195112 A1 | 8/2008 | Liu et al. |
| 2008/0208260 A1 | 8/2008 | Truckai et al. |
| 2009/0024161 A1 | 1/2009 | Bonutti et al. |
| 2009/0275995 A1 | 11/2009 | Truckai et al. |
| 2010/0055646 A1 | 3/2010 | Zhao |
| 2010/0145397 A1 | 6/2010 | Overes et al. |
| 2012/0022092 A1 | 1/2012 | Trieu |

FOREIGN PATENT DOCUMENTS

| | | |
|---|---|---|
| EP | 0701824 | 3/1996 |
| EP | 1366774 | 12/2003 |
| WO | 2002058592 | 8/2002 |
| WO | 2002064062 | 8/2002 |
| WO | 2002087416 | 11/2002 |
| WO | 2004071543 | 8/2004 |
| WO | 2004075954 | 2/2005 |
| WO | 2006031490 | 3/2006 |
| WO | 2006062916 | 6/2006 |
| WO | 2006062939 | 6/2006 |
| WO | 2006090379 | 8/2006 |
| WO | 2007015202 | 2/2007 |
| WO | 2006130491 | 3/2007 |
| WO | 2007028120 | 3/2007 |
| WO | 2008097855 | 8/2008 |
| WO | 2008125049 | 10/2008 |
| WO | 2009108893 | 9/2009 |

OTHER PUBLICATIONS

European Examination Report dated Sep. 18, 2009 for EP05848386.8.
European Search Report dated Aug. 8, 2015 for EP15167203.7.
European Search Report dated Aug. 27, 2015 for EP15167203.
European Search Report dated Oct. 18, 2011 for EP11007504.
Final Office Action in U.S. Appl. No. 11/196,089 dated May 8, 2009.
International Search Report and Written Opinion dated Apr. 22, 2010 for PCT/US2009/035549.
International Search Report and Written Opinion dated May 31, 2006 for PCT/US2005/044055.

(56) References Cited

OTHER PUBLICATIONS

International Search Report and Written Opinion dated Jun. 20, 2006 for PCT/US2005/043984.
Notice of Allowance dated Dec. 14, 2016 for U.S. Appl. No. 14/683,506.
Office Action dated Jan. 3, 2008 for U.S. Appl. No. 11/196,089.
Office Action dated Jan. 3, 2008 for U.S. Appl. No. 11/209,035.
Office Action dated Feb. 28, 2008 for U.S. Appl. No. 11/148,973.
Office Action dated Mar. 20, 2008 for U.S. Appl. No. 11/165,652.
Office Action dated Mar. 24, 2008 for U.S. Appl. No. 11/165,651.
Office Action dated Jun. 29, 2007 for U.S. Appl. No. 11/148,973.
Office Action dated Sep. 18, 2008 for U.S. Appl. No. 11/209,035.
Office Action dated Sep. 21, 2007 for U.S. Appl. No. 11/165,651.
Office Action dated Sep. 22, 2008 for U.S. Appl. No. 11/165,651.
Office Action dated Sep. 26, 2016 for U.S. Appl. No. 14/683,506.
Office Action dated Oct. 3, 2007 for U.S. Appl. No. 11/165,652.
Dthce Action dated Oct. 3, 2008 for U.S. Appl. No. 11/196,045.
Office Action dated Nov. 27, 2009 for U.S. Appl. No. 11/148,973.
Office Action dated Nov. 30, 2007 for U.S. Appl. No. 11/208,448.
Office Action dated Dec. 28, 2009 for U.S. Appl. No. 11/196,089.
Office Action in U.S. Appl. No. 11/148,973 dated Apr. 16, 2009.
Office Action in U.S. Appl. No. 11/148,973 dated Sep. 26, 2008.
Office Action in U.S. Appl. No. 11/196,045 dated Apr. 3, 2009.
Office Action in U.S. Appl. No. 11/196,045, dated Jan. 7, 2010
Office Action in U.S. Appl. No. 11/208,448 dated Apr. 3, 2009.
Office Action in U.S. Appl. No. 11/208,448, dated Dec. 29, 2009.
Office Action in U.S. Appl. No. 11/209,035 dated May 20, 2009.
Office Action in U.S. Appl. No. 11/209,035, dated Sep. 18, 2008.
Office Action U.S. Appl. No. 11/165,652 dated Sep. 19, 2008, dated Sep. 19, 2008.
Office Action dated Sep. 19, 2008 for U.S. Appl. No. 11/196,089, dated Sep. 19, 2008.
Final Office Action dated Sep. 8, 2008 for U.S. Appl. No. 11/208,448, filed Sep. 8, 2008.
Am J Neuroradiol 25(2) ,Feb. 2004 ,175-180.
'Bone Treatment Systems and Methods, U.S. Appl. No. 11/165,651, filed Jun. 24, 2005 Listing of Claims as of Dec. 19, 2008 , Jun. 24, 2005 ,1-6.
'Final Office Action, U.S. Appl. No. 11/165,652, filed Jun. 24, 2005 , dated Mar. 20, 2008 ,1-10.
'Final Office Action, Final Office Action in U.S. Appl. No. 11/165,651 dated Mar. 24, 2008 , dated Mar. 24, 2008 ,1-14.
'International Search Report, PCT/US2005/044055 , dated Jun. 12, 2005 ,1-4.
'International Search Report, PCT/US05/43984 , dated Jun. 20, 2006 ,1-2.
'International Search Report, PCT/US2005/043984 , dated Jun. 20, 2006 ,7 pgs.
'Non-Final Office Action, U.S. App. No. 11/209,035 dated Jan. 3, 2008 , dated Jan. 3, 2008 ,1-12.
'Non-Final Office Action, U.S. Appl. No. 11/165,652, filed Jun. 24, 2005, dated Oct. 3, 2007, 1-9.
'Non-Final Office Action, U.S. Appl. No. 11/208,448 dated Nov. 30, 2007 , dated Nov. 30, 2007 ,1-10.
'Notice of Allowance, Notice of Allowance in U.S. Appl. No. 11/208,448 dated Feb. 19, 2010.
'Notice of Allowance, Notice of Allowance in U.S. Appl. No. 11/209,035 dated Mar. 11, 2010.
'Notice of Allowance and Fees Due, U.S. Appl. No. 11/165,652, filed Jun. 24, 2005 , dated Apr. 17, 2009 ,1-2.
'Office Action, Office Action in U.S. Appl. No. 11/209,035 dated May 20, 2009 ,12.
Bernhard, et al., Asymptomatic Diffuse Pulmonary Embolism Caused by Acrylic Cement: An Unusual Complication of Percutaneous Vertebroplasty, Am Rheum Dis; 62 ,2003 ,85-86.
Carrodeguas, et al., Injectable Acrylic Bone Cements for Vertebroplasty with Improved Properties, Journal of Biomedical Research, XP002312783, vol. 68, No. 1 ,Jan. 15, 2004 ,94-104.
Do,Hyun-Woo et al., The Analysis of Polymethylmethacraylate Leakage After Vertebroplasty for Vertebral Body compression Fractures, Jour of Korean Neurosurg Soc, vol. 35 No. 5 (hhttp://www.jkns.or.kr/htm/abstract.asp?no=0042004086) ,May 2004 ,478-482.
Furderer, et al., Vertebral Body Stenting. A Method for Repositioning and Augmenting Vertebral Compression Fractures, Orthopade, 31(4) ,Apr. 2002 ,356-361.
Groen, et al., Anatomical and Patyhological Considerations in Percutaneous Vertebroplasty and Kyphoplasty: A Reappraisal of the Vertebral Venous System, Spine, vol. 29 No. 13 ,2004 ,1465-1471.
Heublein, et al., Biocorrosion of Mangesium Alloys: A New Principle in Cardiovascular Implant Technology, Heart, 89 ,2003 ,651-656.
Kirby, et al., Acute Bronchospasm Due to Exposure to Polymethylmethacrylate Vapors During Percutaneous Vertebroplasty, Am J Roentgenol, 180 ,2003 ,543-544.

* cited by examiner

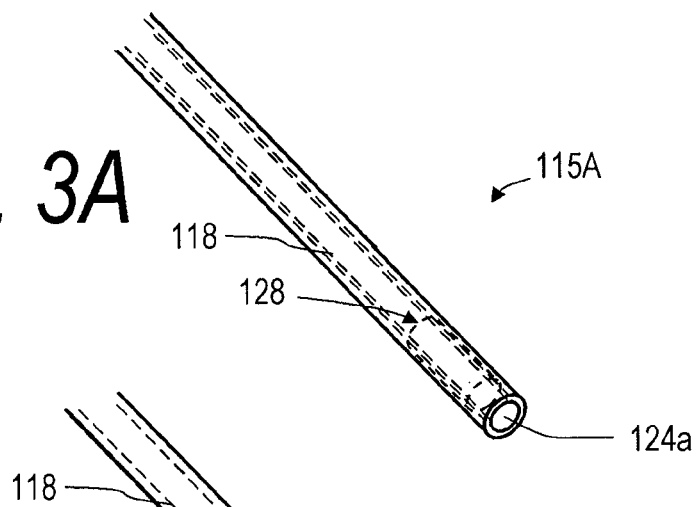
FIG. 3A
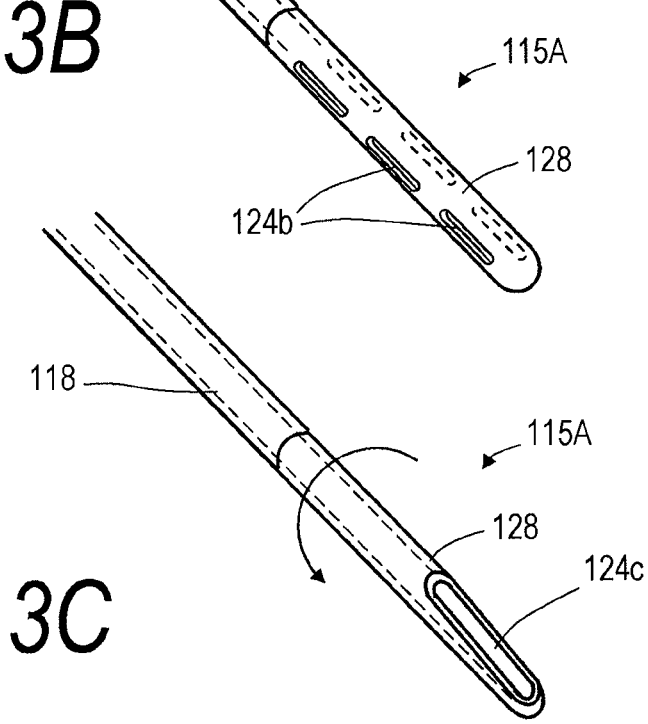
FIG. 3B
FIG. 3C

BONE TREATMENT SYSTEMS AND METHODS

CROSS-REFERENCE TO RELATED APPLICATIONS

This application is a continuation of U.S. application Ser. No. 14/683,506, filed Apr. 10, 2015, which is a continuation of U.S. application Ser. No. 13/734,829, filed Jan. 4, 2013, now U.S. Pat. No. 9,005,210, which is a continuation of U.S. application Ser. No. 12/786,362, filed May 24, 2010, now U.S. Pat. No. 8,348,955, which is a continuation of U.S. application Ser. No. 11/209,035, filed Aug. 22, 2005, now U.S. Pat. No. 7,722,620, which is a continuation-in-part of U.S. application Ser. No. 11/208,448, filed Aug. 20, 2005, now U.S. Pat. No. 7,717,918, which is a continuation-in-part of U.S. application Ser. No. 11/196,045, filed Aug. 2, 2005, now U.S. Pat. No. 8,070,753, which is a continuation-in-part of U.S. application Ser. No. 11/165,652, filed Jun. 24, 2005, now U.S. Pat. No. 7,559,932, which claims the benefit of U.S. Provisional Application Ser. No. 60/633,509, filed Dec. 6, 2004. This application is also related to U.S. patent application Ser. No. 11/165,651, filed Jun. 24, 2005, now U.S. Pat. No. 7,678,116. The entire contents of all of the above applications are hereby incorporated by reference and should be considered a part of this specification.

BACKGROUND OF THE INVENTION

Field of the Invention

The present invention relates in certain embodiments to medical devices for treating osteoplasty procedures such as vertebral compression fractures. More particularly, embodiments of the invention relate to instruments and methods for controllably restoring vertebral body height by controlling bone cement flows into the interior of a vertebra. An exemplary system utilizes Rf energy in combination a conductive bone cement and a controller for controlling cement flow parameters and energy delivery parameters to provide pulsed cement flows with high acceleration rates for applying expansion forces to the bone and for controlling the geometry of the bone cement.

Description of the Related Art

Osteoporotic fractures are prevalent in the elderly, with an annual estimate of 1.5 million fractures in the United States alone. These include 750,000 vertebral compression fractures (VCFs) and 250,000 hip fractures. The annual cost of osteoporotic fractures in the United States has been estimated at $13.8 billion. The prevalence of VCFs in women age 50 and older has been estimated at 26%. The prevalence increases with age, reaching 40% among 80-year-old women. Medical advances aimed at slowing or arresting bone loss from aging have not provided solutions to this problem. Further, the population affected will grow steadily as life expectancy increases. Osteoporosis affects the entire skeleton but most commonly causes fractures in the spine and hip. Spinal or vertebral fractures also cause other serious side effects, with patients suffering from loss of height, deformity and persistent pain which can significantly impair mobility and quality of life. Fracture pain usually lasts 4 to 6 weeks, with intense pain at the fracture site. Chronic pain often occurs when one vertebral level is greatly collapsed or multiple levels are collapsed.

Postmenopausal women are predisposed to fractures, such as in the vertebrae, due to a decrease in bone mineral density that accompanies postmenopausal osteoporosis. Osteoporosis is a pathologic state that literally means "porous bones". Skeletal bones are made up of a thick cortical shell and a strong inner meshwork, or cancellous bone, of with collagen, calcium salts and other minerals. Cancellous bone is similar to a honeycomb, with blood vessels and bone marrow in the spaces. Osteoporosis describes a condition of decreased bone mass that leads to fragile bones which are at an increased risk for fractures. In an osteoporosis bone, the sponge-like cancellous bone has pores or voids that increase in dimension making the bone very fragile. In young, healthy bone tissue, bone breakdown occurs continually as the result of osteoclast activity, but the breakdown is balanced by new bone formation by osteoblasts. In an elderly patient, bone resorption can surpass bone formation thus resulting in deterioration of bone density. Osteoporosis occurs largely without symptoms until a fracture occurs.

Vertebroplasty and kyphoplasty are recently developed techniques for treating vertebral compression fractures. Percutaneous vertebroplasty was first reported by a French group in 1987 for the treatment of painful hemangiomas. In the 1990's, percutaneous vertebroplasty was extended to indications including osteoporotic vertebral compression fractures, traumatic compression fractures, and painful vertebral metastasis. Vertebroplasty is the percutaneous injection of PMMA (polymethylmethacrylate) into a fractured vertebral body via a trocar and cannula. The targeted vertebrae are identified under fluoroscopy. A needle is introduced into the vertebrae body under fluoroscopic control, to allow direct visualization. A bilateral transpedicular (through the pedicle of the vertebrae) approach is typical but the procedure can be done unilaterally. The bilateral transpedicular approach allows for more uniform PMMA infill of the vertebra.

In a bilateral approach, approximately 1 to 4 ml of PMMA is used on each side of the vertebra. Since the PMMA needs to be is forced into the cancellous bone, the techniques require high pressures and fairly low viscosity cement. Since the cortical bone of the targeted vertebra may have a recent fracture, there is the potential of PMMA leakage. The PMMA cement contains radiopaque materials so that when injected under live fluoroscopy, cement localization and leakage can be observed. The visualization of PMMA injection and extravasation are critical to the technique—and the physician terminates PMMA injection when leakage is evident. The cement is injected using syringes to allow the physician manual control of injection pressure.

Kyphoplasty is a modification of percutaneous vertebroplasty. Kyphoplasty involves a preliminary step consisting of the percutaneous placement of an inflatable balloon tamp in the vertebral body. Inflation of the balloon creates a cavity in the bone prior to cement injection. The proponents of percutaneous kyphoplasty have suggested that high pressure balloon-tamp inflation can at least partially restore vertebral body height. In kyphoplasty, some physicians state that PMMA can be injected at a lower pressure into the collapsed vertebra since a cavity exists, when compared to conventional vertebroplasty.

The principal indications for any form of vertebroplasty are osteoporotic vertebral collapse with debilitating pain. Radiography and computed tomography must be performed in the days preceding treatment to determine the extent of vertebral collapse, the presence of epidural or foraminal stenosis caused by bone fragment retropulsion, the presence of cortical destruction or fracture and the visibility and degree of involvement of the pedicles.

Leakage of PMMA during vertebroplasty can result in very serious complications including compression of adjacent structures that necessitate emergency decompressive surgery. See "Anatomical and Pathological Considerations in Percutaneous Vertebroplasty and Kyphoplasty: A Reappraisal of the Vertebral Venous System", Groen, R. et al, Spine Vol. 29, No. 13, pp 1465-1471 2004. Leakage or extravasion of PMMA is a critical issue and can be divided into paravertebral leakage, venous infiltration, epidural leakage and intradiscal leakage. The exothermic reaction of PMMA carries potential catastrophic consequences if thermal damage were to extend to the dural sac, cord, and nerve roots. Surgical evacuation of leaked cement in the spinal canal has been reported. It has been found that leakage of PMMA is related to various clinical factors such as the vertebral compression pattern, and the extent of the cortical fracture, bone mineral density, the interval from injury to operation, the amount of PMMA injected and the location of the injector tip. In one recent study, close to 50% of vertebroplasty cases resulted in leakage of PMMA from the vertebral bodies. See Hyun-Woo Do et al, "The Analysis of Polymethylmethacrylate Leakage after Vertebroplasty for Vertebral Body Compression Fractures", Jour. of Korean Neurosurg. Soc. Vol. 35, No. 5 (May 2004) pp. 478-82, (http://www.jkns.or.kr/htm/abstract.asp?no=0042004086).

Another recent study was directed to the incidence of new VCFs adjacent to the vertebral bodies that were initially treated. Vertebroplasty patients often return with new pain caused by a new vertebral body fracture. Leakage of cement into an adjacent disc space during vertebroplasty increases the risk of a new fracture of adjacent vertebral bodies. See Am. J. Neuroradiol. 2004 Febuary; 25(2):175-80. The study found that 58% of vertebral bodies adjacent to a disc with cement leakage fractured during the follow-up period compared with 12% of vertebral bodies adjacent to a disc without cement leakage.

Another life-threatening complication of vertebroplasty is pulmonary embolism. See Bernhard, J. et al, "Asymptomatic diffuse pulmonary embolism caused by acrylic cement: an unusual complication of percutaneous vertebroplasty", Ann. Rheum. Dis. 2003; 62:85-86. The vapors from PMMA preparation and injection also are cause for concern. See Kirby, B, et al., "Acute bronchospasm due to exposure to polymethylmethacrylate vapors during percutaneous vertebroplasty", Am. J. Roentgenol. 2003; 180:543-544.

In both higher pressure cement injection (vertebroplasty) and balloon-tamped cementing procedures (kyphoplasty), the methods do not provide for well controlled augmentation of vertebral body height. The direct injection of bone cement simply follows the path of least resistance within the fractured bone. The expansion of a balloon applies also compacting forces along lines of least resistance in the collapsed cancellous bone. Thus, the reduction of a vertebral compression fracture is not optimized or controlled in high pressure balloons as forces of balloon expansion occur in multiple directions.

In a kyphoplasty procedure, the physician often uses very high pressures (e.g., up to 200 or 300 psi) to inflate the balloon which crushes and compacts cancellous bone. Expansion of the balloon under high pressures close to cortical bone can fracture the cortical bone, typically the endplates, which can cause regional damage to the cortical bone with the risk of cortical bone necrosis. Such cortical bone damage is highly undesirable as the endplate and adjacent structures provide nutrients for the disc.

Kyphoplasty also does not provide a distraction mechanism capable of 100% vertebral height restoration. Further, the kyphoplasty balloons under very high pressure typically apply forces to vertebral endplates within a central region of the cortical bone that may be weak, rather than distributing forces over the endplate.

There is a general need to provide bone cements and methods for use in treatment of vertebral compression fractures that provide a greater degree of control over introduction of cement and that provide better outcomes. The present invention meets this need and provides several other advantages in a novel and nonobvious manner.

SUMMARY OF THE INVENTION

Certain embodiments of the invention provide systems and methods for utilizing Rf energy in combination with a bone cement that carries an electrically conductive filler. A computer controller controls cement inflow parameters and energy delivery parameters for selectively polymerizing the cement inflow plume to thereby control the direction of flow and the ultimate geometry of a flowable, in-situ hardenable cement composite. The system and method further includes means for sealing tissue in the interior of a vertebra to prevent migration of monomers, fat or emboli into the patient's bloodstream.

These and other objects of the present invention will become readily apparent upon further review of the following drawings and specification.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

FIG. 3A is a schematic perspective view of a working end of a probe, in accordance with one embodiment.

FIG. 3B is a schematic perspective view of a working end of a probe, in accordance with another embodiment.

FIG. 3C is a schematic perspective view of a working end of a probe, in accordance with yet another embodiment.

DETAILED DESCRIPTION OF THE PREFERRED EMBODIMENT

Figure 1:
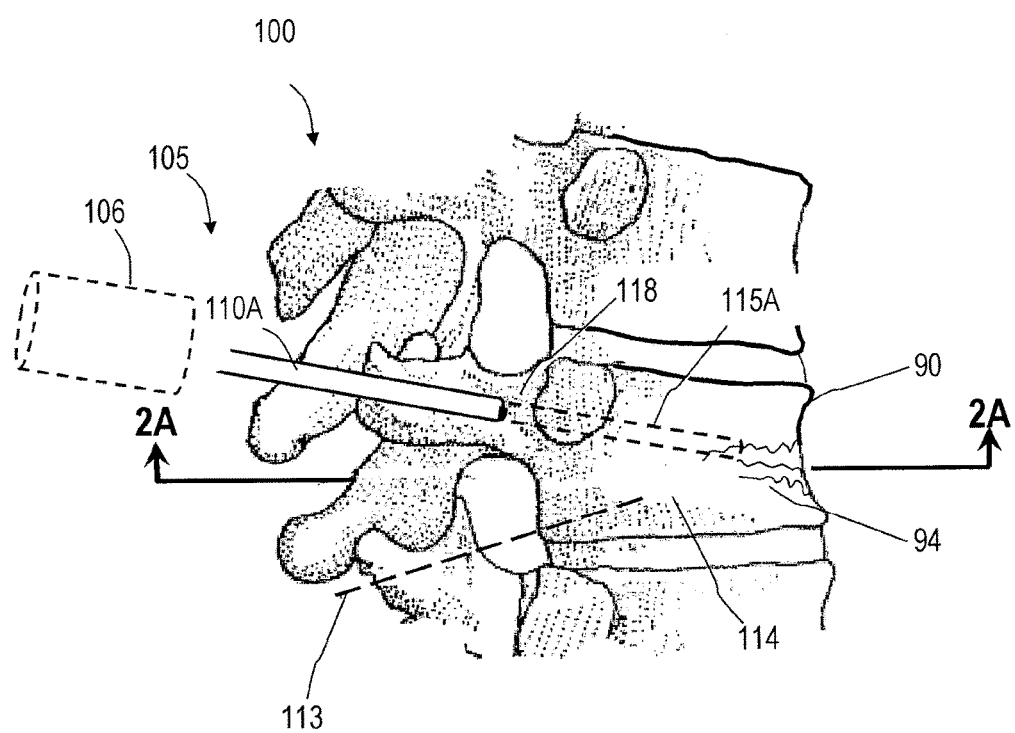
FIG. 1 is a schematic side view of a spine segment showing a vertebra with a compression fracture and an introducer, in accordance with one embodiment disclosed herein.

FIG. 1 illustrates one embodiment of the invention for treating a spine segment in which a vertebral body 90 has a wedge compression fracture indicated at 94. In one embodiment, the systems and methods of the invention are directed to safely introducing a bone fill material into cancellous bone of the vertebra without extravasion of fill material in unwanted directions (i) to prevent micromotion in the fracture for eliminating pain, and (ii) to support the vertebra and increase vertebral body height. Further, the invention includes systems and methods for sealing cancellous bone (e.g., blood vessels, fatty tissues etc.) in order to prevent monomers, fat, fill material and other emboli from entering the venous system during treatment.

Figure 2A:
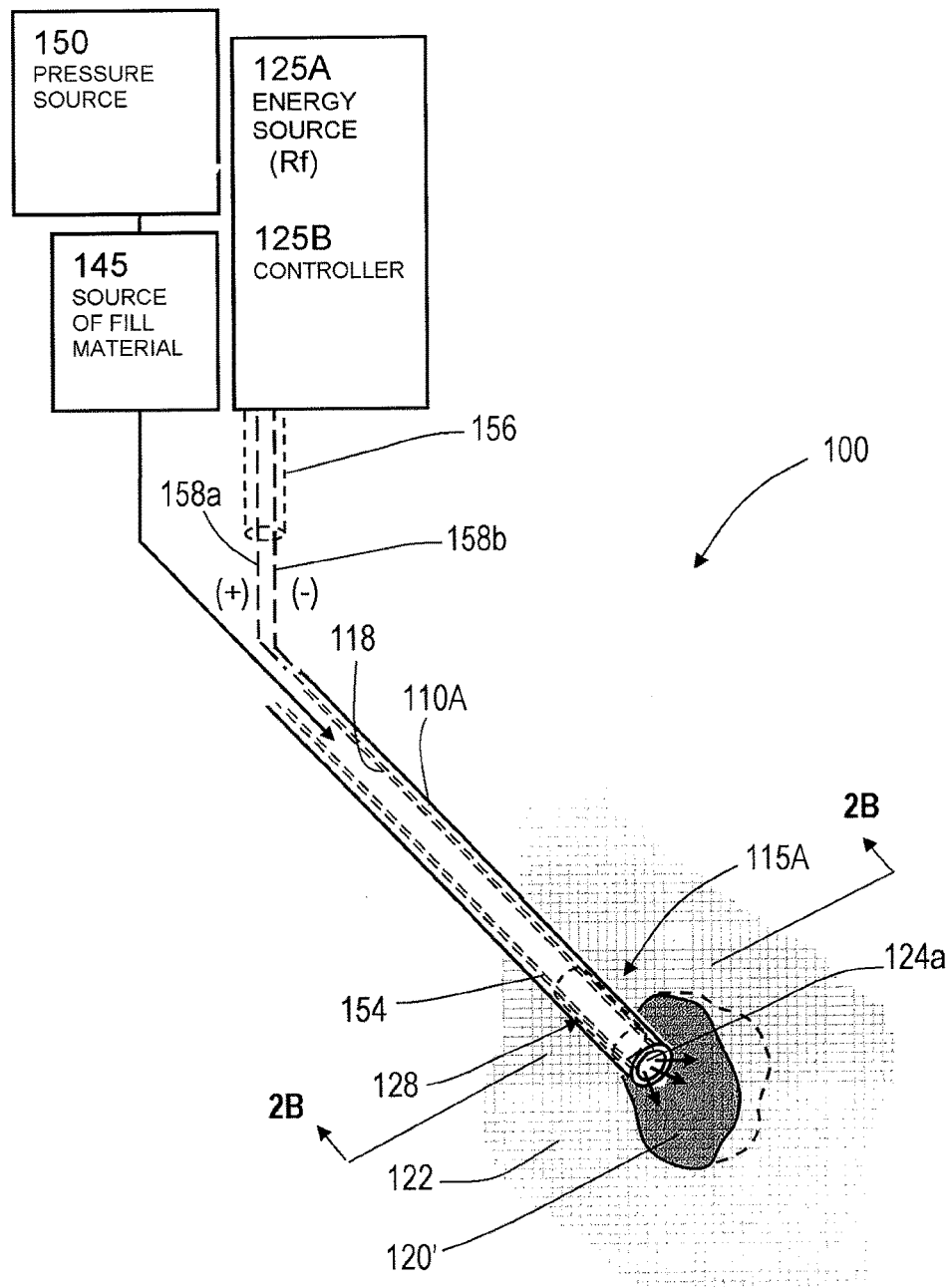
FIG. 2A is a schematic perspective view of a system for treating bone, in accordance with one embodiment.

FIG. 1 illustrates a fractured vertebra and bone infill system 100 which includes probe 105 having a handle end 106 extending to an elongated introducer 110A and working end 115A, shown in FIG. 2A. The introducer is shown introduced through pedicle 118 of the vertebra for accessing the osteoporotic cancellous bone 122 (See FIG. 2A). The initial aspects of the procedure are similar to conventional percutaneous vertebroplasty wherein the patient is placed in a prone position on an operating table. The patient is typically under conscious sedation, although general anesthesia is an alternative. The physician injects a local anesthetic (e.g., 1% Lidocaine) into the region overlying the targeted pedicle or pedicles as well as the periosteum of the pedicle(s). Thereafter, the physician uses a scalpel to make a 1 to 5 mm skin incision over each targeted pedicle. Thereafter, the introducer 110A is advanced through the pedicle into the anterior region of the vertebral body, which typically is the region of greatest compression and fracture. The physician confirms the introducer path posterior to the pedicle, through the pedicle and within the vertebral body by anteroposterior and lateral X-Ray projection fluoroscopic views. The introduction of infill material as described below can be imaged several times, or continuously, during the treatment depending on the imaging method.

It should be appreciated that the introducer also can be introduced into the vertebra from other angles, for example, along axis 113 through the wall of the vertebral body 114 as in FIG. 1 or in an anterior approach (not shown). Further, first and second cooperating introducers can be used in a bilateral transpedicular approach. Additionally, any mechanism known in the art for creating an access opening into the interior of the vertebral body 90 can be used, including open surgical procedures.

Definitions

"Bone fill material, infill material or composition" includes its ordinary meaning and is defined as any material for infilling a bone that includes an in-situ hardenable material. The fill material also can include other "fillers" such as filaments, microspheres, powders, granular elements, flakes, chips, tubules and the like, autograft or allograft materials, as well as other chemicals, pharmacological agents or other bioactive agents.

"Flowable material" includes its ordinary meaning and is defined as a material continuum that is unable to withstand a static shear stress and responds with an irrecoverable flow (a fluid)—unlike an elastic material or elastomer that responds to shear stress with a recoverable deformation. Flowable material includes fill material or composites that include a fluid (first) component and an elastic or inelastic material (second) component that responds to stress with a flow, no matter the proportions of the first and second component, and wherein the above shear test does not apply to the second component alone.

An "elastomer" includes its ordinary meaning and is defined as material having to some extent the elastic properties of natural rubber wherein the material resumes or moves toward an original shape when a deforming force is removed.

"Substantially" or "substantial" mean largely but not entirely. For example, substantially may mean about 10% to about 99.999%, about 25% to about 99.999% or about 50% to about 99.999%.

"Osteoplasty" includes its ordinary meaning and means any procedure wherein fill material is delivered into the interior of a bone.

"Vertebroplasty" includes its ordinary meaning and means any procedure wherein fill material is delivered into the interior of a vertebra.

Figure 2B:
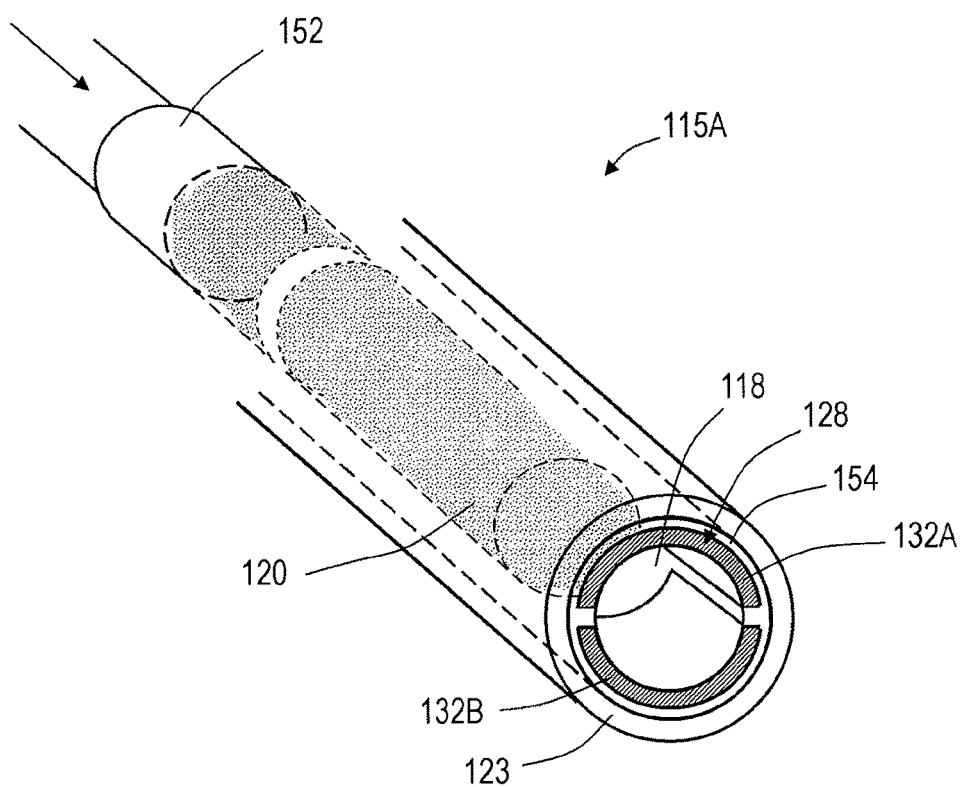
FIG. 2B is a schematic perspective sectional view of a working end of the introducer taken along line 2B-2B of FIG. 2A.

Now referring to FIGS. 2A and 2B, the end of introducer 110A is shown schematically after being introduced into cancellous bone 122 with an inflow of fill material indicated at 120. The cancellous bone can be in any bone, for example in a vertebra. It can be seen that the introducer 110A and working end 115A comprise a sleeve or shaft that is preferably fabricated of a metal having a flow channel 118 extending therethrough from the proximal handle end 106 (see FIG. 1). In one embodiment, the introducer shaft is a stainless steel tube 123 having an outside diameter ranging between about 3.5 and 4.5 mm, but other dimensions are possible. As can be seen in FIGS. 2A and 3A, the flow channel 118 can terminate in a single distal open termination or outlet 124a in the working end 115A, or there can be a plurality of flow outlets or ports 124b configured angularly about the radially outward surfaces of the working end 115A of FIG. 3B. The outlets in the working end thus allow for distal or radial ejection of fill material, or a working end can have a combination of radial and distal end outlets. As can be seen in FIG. 3C, the distal end of working end 115A also can provide an angled distal end outlet 124c for directing the flow of fill material from the outlet by rotating the working end.

In FIGS. 2A and 2B, it can be seen that system 100 includes a remote energy source 125A and a controller 125B that are operatively coupled to an energy emitter 128 in working end 115A for applying energy to fill material 120 contemporaneous with and subsequent to ejection of the fill material from the working end. As shown in FIG. 2A, a preferred energy source 125A is a radiofrequency (Rf) source known in the art that is connected to at least one electrode (132a and 132b in FIGS. 2A and 2B) in contact with injected fill material 120 that carries a radiosensitive composition therein. It is equally possible to use other remote energy sources and emitters 128 in the working end which fall within the scope of the invention, such as (i) an electrical source coupled to a resistive heating element in the working end, (ii) a light energy source (coherent or broadband) coupled to an optical fiber or other light channel terminating in the working end; (iii) an ultrasound source coupled to an emitter in the working end; or a (iv) or a microwave source coupled to an antenna in the working end. In still another embodiment, the energy source can be a magnetic source. The fill material is configured with an energy-absorbing material or an energy-transmitting material that cooperates with energy delivery from a selected energy source. For example, the energy-absorbing or energy-transmitting material can be a radiosensitive or conductive material for cooperating with an Rf source, chromophores for cooperating with a light source, ferromagnetic particles for cooperating with a magnetic source, and the like. In one embodiment, the fill material 120 can include a composition having an energy-absorbing property and an energy-transmitting property for cooperating with the remote energy source 125A. For example, the composition can absorb energy from the remote energy source 125A for polymerizing the composite or transmit energy for heating tissue adjacent to the composite.

As can be understood from FIGS. 2A and 2B, the exemplary introducer 110A is operatively coupleable to a source 145 of bone fill material 120 together with a pressure source or mechanism 150 that operates on the source of fill material to deliver the fill material 120 through the introducer 110A into a bone (see arrows). The pressure source 150 can comprise any type of pump mechanism, such as a piston pump, screw pump or other hydraulic pump mechanism. In FIG. 2B, the pump mechanism is shown as a piston or plunger 152 that is slidable in channel 118 of introducer 110A. In one embodiment, the pressure source 150 includes a controller 150B that controls the pressure applied by the pressure source 150. For example, where the pressure source 150 is a piston pump or screw pump that is motor driven, the controller 150B can adjust the motor speed to vary the pressure applied by the pressure source 150 to the inflow of the bone fill material 120. In one embodiment, the controller 150B also controls the volume of the bone fill material 120 that is introduced to a bone portion. In another embodiment, the controller 150B, or a separate controller, can also control the volume of bone fill material 120 introduced into the bone portion. For example, the controller 150B can operate a valve associated with the bone fill source 145 to selectively vary the valve opening, thus varying the volume of bone fill material 120 introduced to the bone portion.

As shown in FIGS. 2A and 2B, the introducer 110A preferably has an electrically and thermally insulative interior sleeve 154 that defines interior flow channel 118. The sleeve can be any suitable polymer known in the art such as PEEK, Teflon™ or a polyimide. As can be seen in FIG. 2B, interior sleeve 154 carries conductive surfaces that function as energy emitter 128, and more particularly comprise spaced apart opposing polarity electrodes 132a and 132b. The electrodes 132a and 132b can have any spaced apart configuration and are disposed about the distal termination of channel 118 or about the surfaces of outlet 124a. The electrode configuration alternatively can include a first electrode in the interior of channel 118 and a second electrode on an exterior of introducer 110A. For example, the metallic sleeve 123 or a distal portion thereof can comprise one electrode. In a preferred embodiment, the electrodes 132a and 132b are connected to Rf energy source 125A and controller 125B by electrical cable 156 with (+) and (−) electrical leads 158a and 158b therein that extend through the insulative sleeve 154 to the opposing polarity electrodes. In one embodiment, the electrical cable 156 is detachably coupled to the handle end 106 of probe 105 by male-female plug (not shown). The electrodes 132a and 132b can be fabricated of any suitable materials known to those skilled in the art, such as stainless steels, nickel-titanium alloys and alloys of gold, silver platinum and the like.

In one embodiment, not shown, the working end 115A can also carry any suitable thermocouple or temperature sensor for providing data to controller 125B relating to the temperature of the fill material 120 during energy delivery. One or more thermocouples may be positioned at the distal tip of the introducer, or along an outer surface of the introducer and spaced from the distal end, in order to provide temperature readings at different locations within the bone. The thermocouple may also be slideable along the length of the introducer. In another embodiment, the working end can have at least one side port (not shown) in communication with a coolant source, the port configured to provide the coolant (e.g., saline) therethrough into the cancellous bone 122 to cool the cancellous bone in response to a temperature reading from the temperature sensor.

Figure 4:
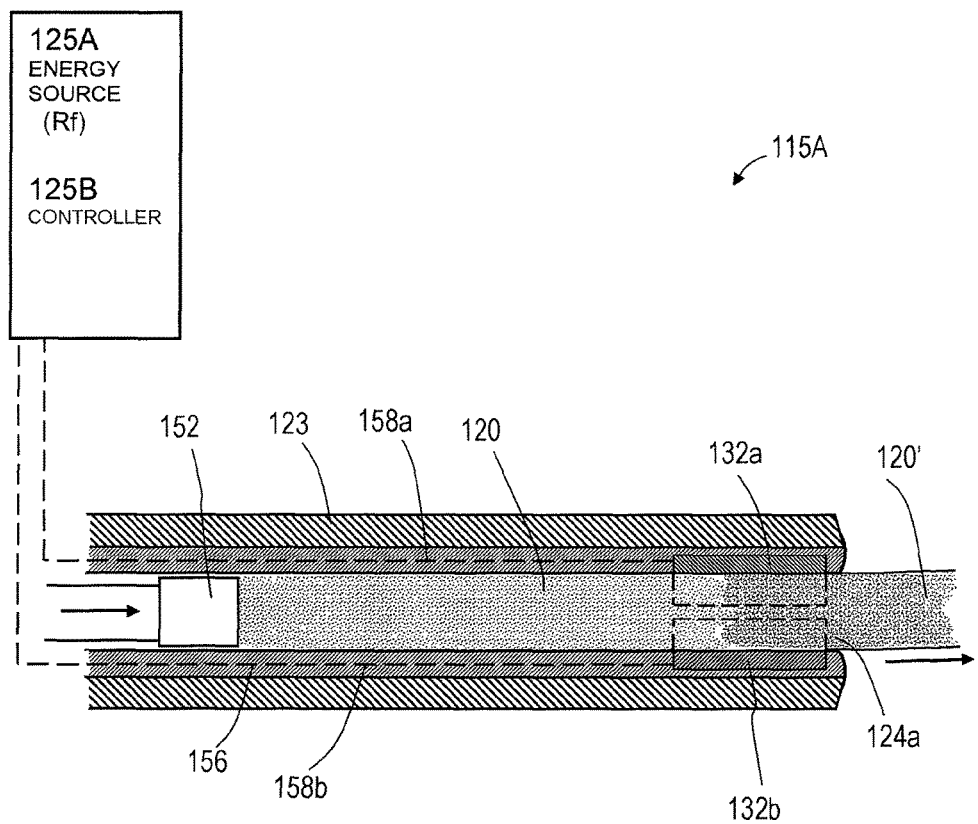
FIG. 4 is a schematic sectional side view of one embodiment of a working end of a probe, in accordance with one embodiment.

Now turning to FIG. 4, the sectional view of working end 115A illustrates the application of energy to fill material 120 as it being ejected from outlet 124a. The fill material 120 in the proximal portion of channel 118 can be a low viscosity flowable material such as a two-part curable polymer that has been mixed (e.g., PMMA) but without any polymerization, for example, having a viscosity of less than about 50,000 cps. Such a low viscosity fill material allows for simplified lower pressure injection through introducer 110A. Further, the system allows the use of a low viscosity fill material 120 which can save great deal of time for the physician.

In a preferred embodiment, it is no longer necessary to wait for the bone cement to partly polymerize before injection. As depicted in FIG. 4, energy delivery at selected parameters from electrodes 132a and 132b to fill material 120 contemporaneous with its ejection from outlet 124a selectively alters a property of fill material indicated at 120'. In one embodiment, the altered flow property is viscosity. For example, the viscosity of the fill material 120' can be increased to a higher viscosity ranging from about 100,000 cps or more, 1,000,000 cps or more, to 2,000,000 cps or more. In another embodiment, the flow property is Young's modulus. For example, the Young's modulus of the fill material 120' can be altered to be between about 10 kPa and about 10 GPa. In still another embodiment, the flow property can be one of durometer, hardness and compliance.

Preferably, the fill material carries a radiosensitive composition for cooperating with the Rf source 125A, as further described below. At a predetermined fill material flow rate and at selected Rf energy delivery parameters, the altered fill material 120' after ejection can comprise an increased viscosity material or an elastomer. At yet another predetermined fill material flow rate and at other Rf energy delivery parameters, the altered fill material 120' after ejection can comprise a substantially solid material. In the system embodiment utilized for vertebroplasty as depicted in FIGS. 2A and 5B, the controller is adapted for delivering Rf energy contemporaneous with the selected flow rate of fill material to provide a substantially high viscosity fill material that is still capable of permeating cancellous bone. In other osteoplasty procedures such as treating necrosis of a bone, the system controller 125B can be adapted to provide much harder fill material 120' upon ejection from outlet 124a. Further, the system can be adapted to apply Rf energy to the fill material continuously, or in a pulse mode or in any selected intervals based on flow rate, presets, or in response to feedback from temperature sensors, impedance measurements or other suitable signals known to those skilled in the art.

In one embodiment, the controller 125B includes algorithms for adjusting power delivery applied by the energy source 125A. For example, in one embodiment the controller 125B includes algorithms for adjusting power delivery based on impedance measurements of the fill material 120' introduced to the bone portion. In another embodiment, the controller 125B includes algorithms for adjusting power delivery based on the volume of bone fill material 120 delivered to the bone portion. In still another embodiment, the controller 125B includes algorithms for adjusting power delivery based on the temperature of the bone fill material 120' introduced to the bone portion.

Figure 5A:
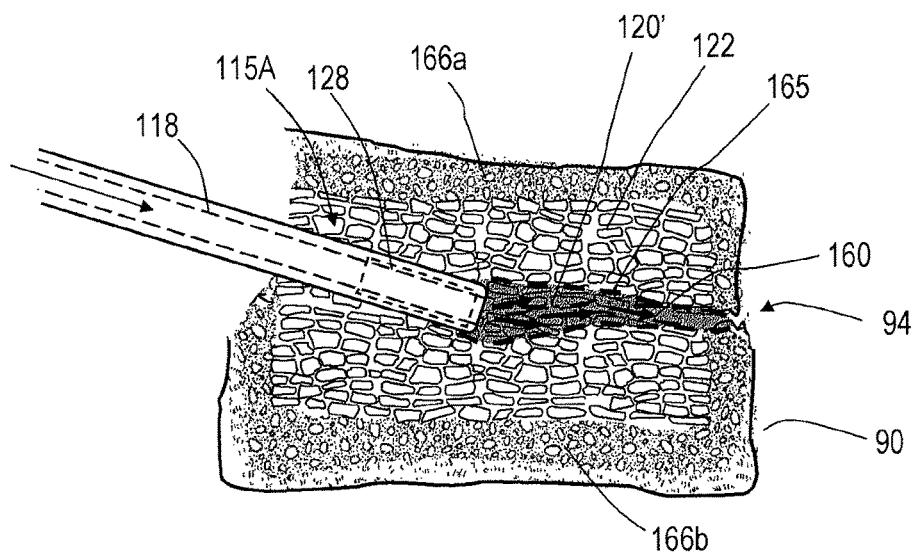
FIG. 5A is a schematic side view of a probe inserted into a vertebral body and injecting flowable fill material into the vertebral body.
Figure 5B:
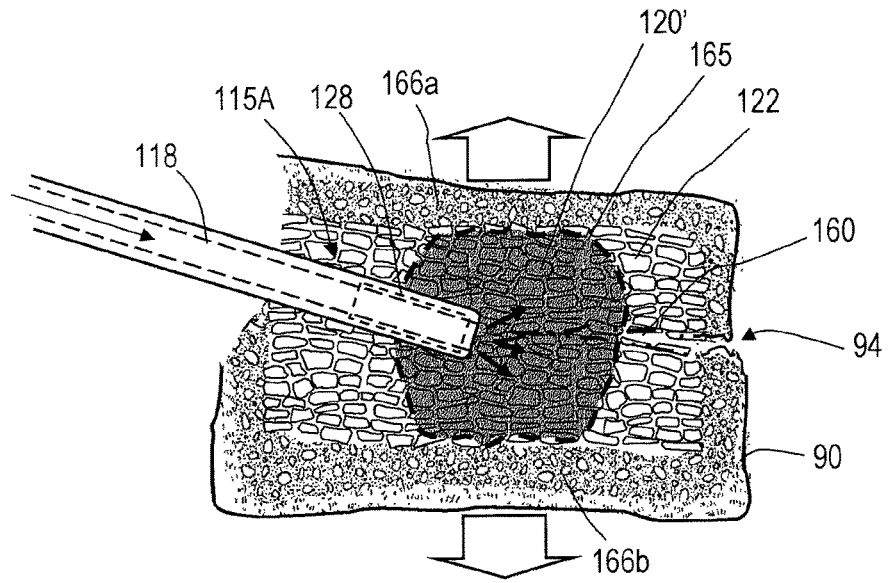
FIG. 5B is a schematic side view of the probe in FIG. 5A injecting a relatively high viscosity volume of flowable fill material into the vertebral body, in accordance with one embodiment of the present invention.

FIGS. 5A and 5B are views of a vertebra 90 that are useful for explaining relevant aspects of one embodiment of the invention wherein working end 110A is advanced into the region of fracture 94 in cancellous bone 122. FIG. 5A indicates system 100 being used to inject flow material 120 into the vertebra with the flow material having a viscosity similar to conventional vertebroplasty or kyphoplasty, for example having the consistency of toothpaste. FIG. 5A depicts the situation wherein high pressure injection of a low viscosity material can simply follow paths of least resistance along a recent fracture plane 160 to migrate anteriorly in an uncontrolled manner. The migration of fill material could be any direction, including posteriorly toward the spinal canal or into the disc space depending on the nature of the fracture.

FIG. 5B illustrates system 100 including actuation of Rf source 125A by controller 125B to contemporaneously heat the fill material to eject altered fill material 120' with a selected higher viscosity into cancellous bone 122, such as the viscosities described above. With a selected higher viscosity, FIG. 5B depicts the ability of the system to prevent extravasion of fill material and to controllably permeate and interdigitate with cancellous bone 122, rather than displacing cancellous bone, with a plume 165 that engages cortical bone vertebral endplates 166a and 166b. The fill material broadly engages surfaces of the cortical endplates to distribute pressures over the endplates. In a preferred embodiment, the fill material controllably permeates cancellous bone 122 and is ejected at a viscosity adequate to interdigitate with the cancellous bone 122. Fill material with a viscosity in the range of about 100,000 cps to 2,000,000 cps may be ejected, though even lower or higher viscosities may also be sufficient. The Rf source may selectively increase the viscosity of the fill material by about 10% or more as it is ejected from the introducer 115A. In other embodiments, the viscosity may be increased by about 20%, 50%, 100%, 500% or 1000% or more.

Still referring to FIG. 5B, it can be understood that continued inflows of high viscosity fill material 120' and the resultant expansion of plume 165 will apply forces on endplates 166a and 166b to at least partially restore vertebral height. It should be appreciated that the working end 115A can be translated axially between about the anterior third of the vertebral body and the posterior third of the vertebral body during the injection fill material 120', as well as rotating the working end 115A which can be any of the types described above (FIGS. 3A-3C).

Figure 6:
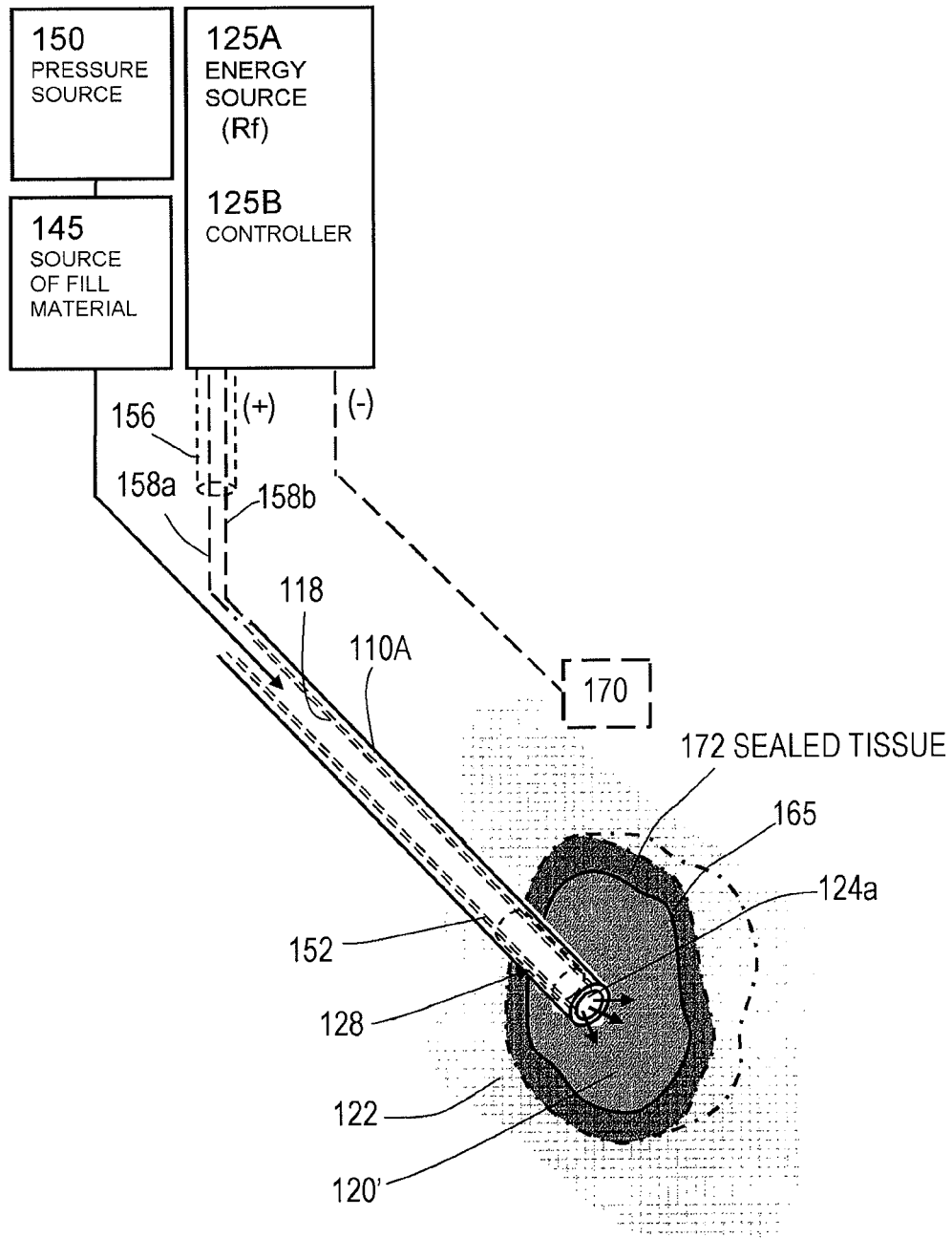
FIG. 6 is a schematic perspective view of a system for treating bone, in accordance with another embodiment.

FIG. 6 is a schematic view of an alternative embodiment of system 100 wherein Rf source 125A and controller 125B are configured to multiplex energy delivery to provide additional functionality. In one mode of operation, the system functions as described above and depicted in FIGS. 4 and 5B to alter flow properties of flowable fill material 120' as it is ejected from working end 115A. As can be seen in FIG. 6, the system further includes a return electrode or ground pad indicated at 170. Thus the system can be operated in a second mode of operation wherein electrodes 132a and 132b are switched to a common polarity (or the distal portion of sleeve 123 can comprise such an electrode) to function in a mono-polar manner in conjunction with ground pad 170. This second mode of operation advantageously creates high energy densities about the surface of plume 165 to thereby ohmically heat tissue at the interface of the plume 165 and the body structure.

In FIG. 6, the ohmically heated tissue is indicated at 172, wherein the tissue effect is coagulation of blood vessels, shrinkage of collagenous tissue and generally the sealing and ablation of bone marrow, vasculature and fat within the cancellous bone. The Rf energy levels can be set at a sufficiently high level to coagulate, seal or ablate tissue, with the controller delivering power based, for example, on impedance feedback which will vary with the surface area of plume 165. Of particular interest, the surface of plume 165 is used as an electrode with an expanding wavefront within cancellous bone 122. Thus, the vasculature within the vertebral body can be sealed by controlled ohmic heating at the same time that fill material 120' is permeating the cancellous bone. Within the vertebral body are the basivertebral (intravertebral) veins which are paired valveless veins connecting with numerous venous channels within the vertebra (pars spongiosa/red bone marrow). These basivertebral veins drain directly into the external vertebral venous plexus (EVVP) and the superior and inferior vena cava. The sealing of vasculature and the basivertebral veins is particularly important since bone cement and monomer embolism has been frequently observed in vertebroplasty and kyphoplasty cases (see "Anatomical and Pathological Considerations in Percutaneous Vertebroplasty and Kyphoplasty: A Reappraisal of the Vertebral Venous System", Groen, R. et al, Spine Vol. 29, No. 13, pp 1465-1471 2004). It can be thus understood that the method of using the system 100 creates and expands a "wavefront" of coagulum that expands as the plume 165 of fill material expands. The expandable coagulum layer 172, besides sealing the tissue from emboli, contains and distributes pressures of the volume of infill material 120' about the plume surface.

The method depicted in FIG. 6 provides an effective means for sealing tissue via ohmic (Joule) heating. It has been found that passive heat transfer from the exothermic reaction of a bone cement does not adequately heat tissue to the needed depth or temperature to seal intravertebral vasculature. In use, the mode of operation of the system 100 in a mono-polar manner for ohmically heating and sealing tissue can be performed in selected intervals alone or in combination with the bi-polar mode of operation for controlling the viscosity of the injected fill material.

In general, one aspect of the vertebroplasty or osteoplasty method in accordance with one of the embodiments disclosed herein allows for in-situ control of flows of a flowable fill material, and more particularly comprises introducing a working end of an introducer sleeve into cancellous bone, ejecting a volume of flowable fill material having a selected viscosity and contemporaneously applying energy (e.g., Rf energy) to the fill material from an external source to thereby increase the viscosity of at least portion of the volume to prevent fill extravasion. In a preferred embodiment, the system increases the viscosity by about 20% or more. In another preferred embodiment, the system increases the viscosity by about 50% or more.

In another aspect of one embodiment of a vertebroplasty method, the system 100 provides means for ohmically heating a body structure about the surface of the expanding plume 165 of fill material to effectively seal intravertebral vasculature to prevent emboli from entering the venous system. The method further provides an expandable layer of coagulum about the infill material to contain inflow pressures and distribute further expansion forces over the vertebral endplates. In a preferred embodiment, the coagulum expands together with at least a portion of the infill material to engage and apply forces to endplates of the vertebra.

Of particular interest, one embodiment of fill material 120 as used in the systems described herein (see FIGS. 2A, 4, 5A-5B and 6) is a composite comprising an insitu hardenable or polymerizable cement component 174 and an electrically conductive filler component 175 in a sufficient volume to enable the composite to function as a dispersable electrode (FIG. 6). In one type of composite, the conductive filler component is any biocompatible conductive metal. In another type of composite, the conductive filler component is a form of carbon. The biocompatible metal can include at least one of titanium, tantalum, stainless steel, silver, gold, platinum, nickel, tin, nickel titanium alloy, palladium, magnesium, iron, molybdenum, tungsten, zirconium, zinc, cobalt or chromium and alloys thereof. The conductive filler component has the form of at least one of filaments, particles, microspheres, spheres, powders, grains, flakes, granules, crystals, rods, tubules, nanotubes, scaffolds and the like. In one embodiment, the conductive filler includes carbon nanotubes. Such conductive filler components can be at least one of rigid, non-rigid, solid, porous or hollow, with conductive filaments 176a illustrated in FIG. 7A and conductive particles 176b depicted in FIG. 7B.

Figure 7A:
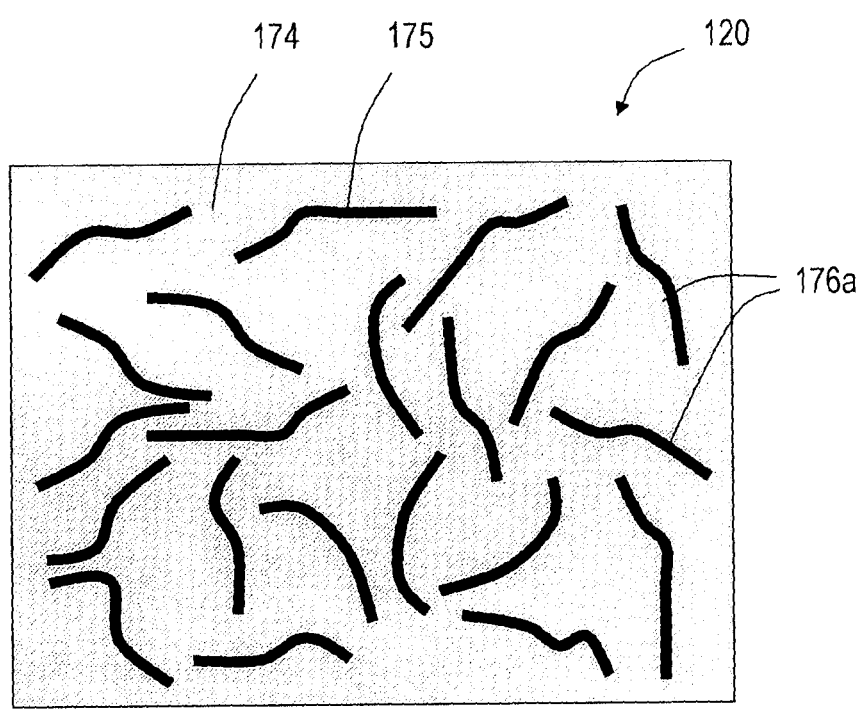
FIG. 7A is a schematic sectional view of a fill material, in accordance with one embodiment.
Figure 7B:
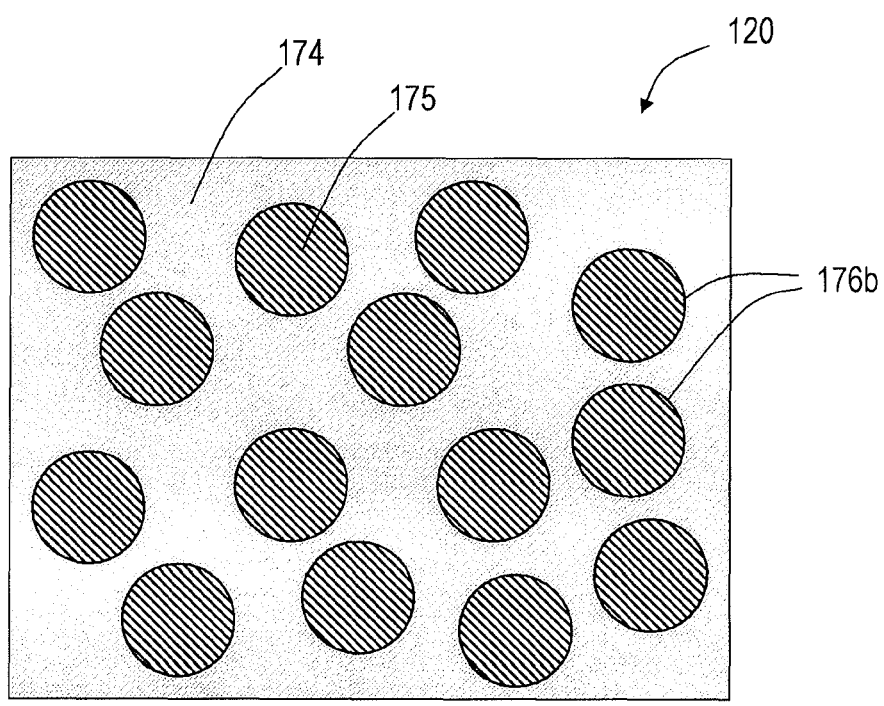
FIG. 7B is a schematic sectional view of a fill material, in accordance with another embodiment.

In a preferred embodiment, the conductive filler comprises chopped microfilaments or ribbons of a metal as in FIG. 7A that have a diameter or a cross-section dimension across a major axis ranging between about 0.0005" and 0.01". The lengths of the microfilaments or ribbons range from about 0.01" to 0.50". The microfilaments or ribbons are of stainless steel or titanium and are optionally coated with a thin gold layer or silver layer that can be deposited by electroless plating methods. Of particular interest, the fill material 120 of FIG. 7A has an in situ hardenable cement component 174 than has a first low viscosity and the addition of the elongated microfilament conductive filler component 175 causes the composite 120 to have a substantially high apparent viscosity due to the high surface area of the microfilaments and its interaction with the cement component 174. In one embodiment, the microfilaments are made of stainless steel, plated with gold, and have a diameter of about 12 microns and a length of about 6 mm. The other dimensions provided above and below may also be utilized for these microfilaments.

In another embodiment of bone fill material 120, the conductive filler component comprises elements that have a non-conductive core portion with a conductive cladding portion for providing electrosurgical functionality. The non-conductive core portions are selected from the group consisting of glass, ceramic or polymer materials. The cladding can be any suitable conductive metal as described above that can be deposited by electroless plating methods.

In any embodiment of bone fill material that uses particles, microspheres, spheres, powders, grains, flakes, granules, crystals or the like, such elements can have a mean dimension across a principal axis ranging from about 0.5 micron to 2000 microns. More preferably, the mean dimension across a principal axis range from about 50 microns to 1000 microns. It has been found that metal microspheres having a diameter of about 800 microns are useful for creating conductive bone cement that can function as an electrode.

In one embodiment, a conductive filler comprising elongated microfilaments wherein the fill material has from about 0.5% to 20% microfilaments by weight. More preferably, the filaments are from about 1% to 10% by weight of the fill material. In other embodiments wherein the conductive filler comprises particles or spheres, the conductive filler can comprise from about 5% of the total weight to about 80% of the weight of the material.

In an exemplary fill material 120, the hardenable component can be any in-situ hardenable composition such as at least one of PMMA, monocalcium phosphate, tricalcium phosphate, calcium carbonate, calcium sulphate or hydroxyapatite.

Figure 8A:
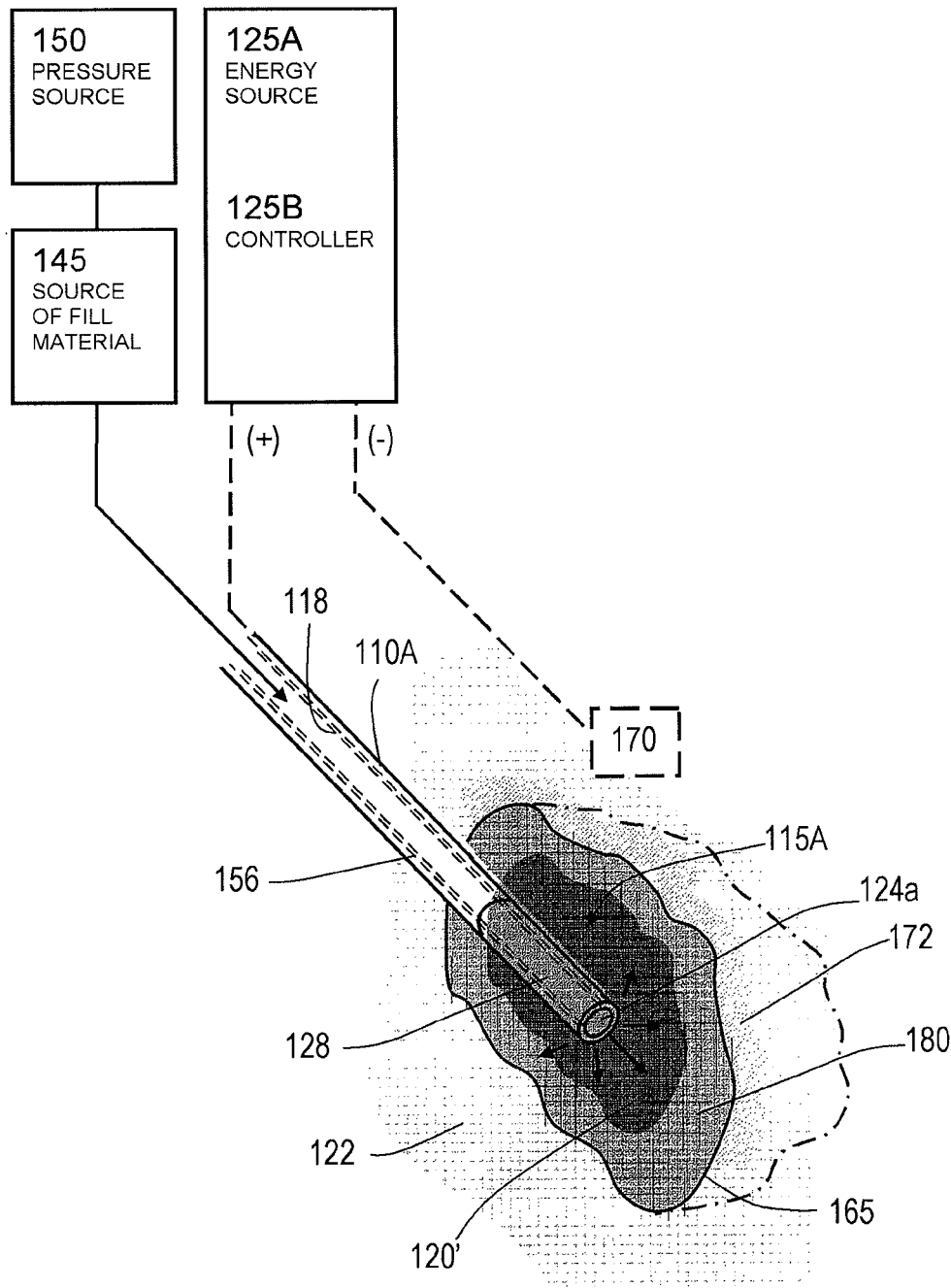
FIG. 8A is a schematic perspective view of a system for treating bone, in accordance with another embodiment.
Figure 8B:
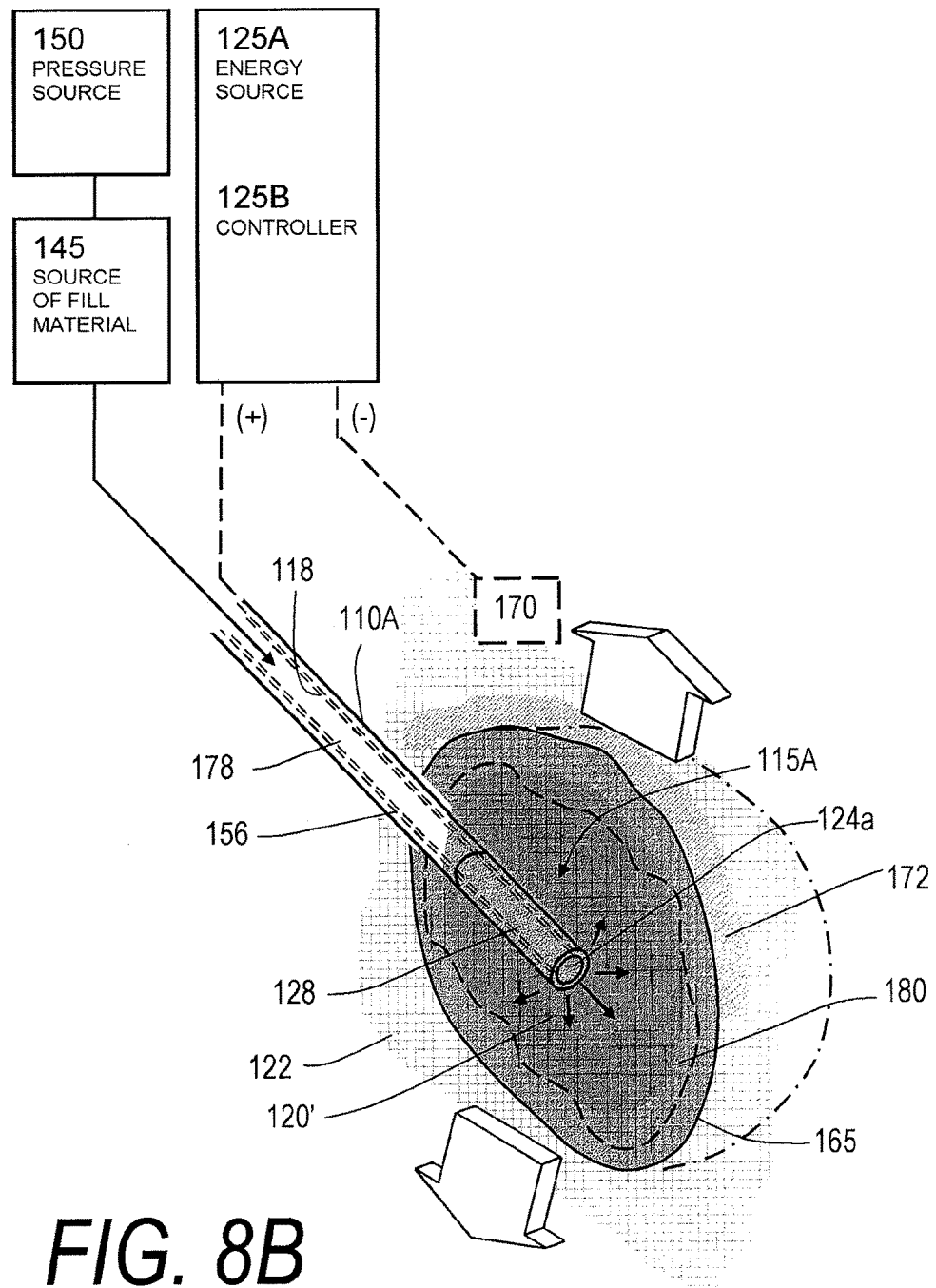
FIG. 8B is a schematic perspective view of the system in FIG. 8A, injecting an additional volume of fill material into a vertebral body.

Referring now to FIGS. 8A and 8B, an alternative method is shown wherein the system 100 and method are configured for creating asymmetries in properties of the infill material and thereby in the application of forces in a vertebroplasty. In FIG. 8A, the pressure mechanism 150 is actuated to cause injection of an initial volume or aliquot of fill material 120' that typically is altered in viscosity in working end 110A as described above—but the method encompasses flows of fill material having any suitable viscosity. The fill material is depicted in FIGS. 8A and 8B as being delivered in a unilateral transpedicular approach, but any extrapedicular posterior approach is possible as well as any bilateral posterior approach. The system in FIGS. 8A-8B again illustrates a vertical plane through the fill material 120' that flows under pressure into cancellous bone 122 with expanding plume or periphery indicated at 165. The plume 165 has a three dimensional configuration as can be seen in FIG. 8B, wherein the pressurized flow may first tend to flow more horizontally that vertically. One embodiment of the method of the invention includes the physician translating the working end slightly and/or rotating the working end so that flow outlets 124a are provided in a selected radial orientation. In a preferred embodiment, the physician intermittently monitors the flows under fluoroscopic imaging as described above.

FIG. 8B depicts a contemporaneous or subsequent energy-delivery step of the method wherein the physician actuates Rf electrical source 125A and controller 125B to cause Rf current delivery from at least one electrode emitter 128 to cause ohmic (Joule) heating of tissue as well as internal heating of the inflowing fill material 120'. In this embodiment, the exterior surface of sleeve 123 is indicated as electrode or emitter 128 with the proximal portion of introducer 110A having an insulator coating 178. The Rf energy is preferably applied in an amount and for a duration that coagulates tissue as well as alters a flowability property of surface portions 180 of the initial volume of fill material proximate the highest energy densities in tissue.

In one preferred embodiment, the fill material 120 is particularly designed to create a gradient in the distribution of conductive filler with an increase in volume of material injected under high pressure into cancellous bone 122. This aspect of the method in turn can be used advantageously to create asymmetric internal heating of the fill volume. In this embodiment, the fill material 120 includes a conductive filler of elongated conductive microfilaments 176a (FIG. 7A). The filaments are from about 2% to 5% by weight of the fill material, with the filaments having a mean diameter or mean sectional dimension across a minor axis ranging between about 0.001" and 0.010" and a length ranging from about 1 mm to about 10 mm, more preferably about 1 mm to 5 mm. In another embodiment, the filaments have a mean diameter or a mean dimension across a minor axis ranging between about 1 micron and 500 microns, more preferably between about 1 micron and 50 microns, even more preferably between about 1 micron and 20 microns. It has been found that elongated conductive microfilaments 176a result in resistance to flows thereabout which causes such microfilaments to aggregate away from the most active media flows that are concentrated in the center of the vertebra proximate to outlet 124a. Thus, the conductive microfilaments 176a attain a higher concentration in the peripheral or surface portion 180 of the plume which in turn will result in greater internal heating of the fill portions having such higher concentrations of conductive filaments. The active flows also are controlled by rotation of introducer 110A to eject the material preferentially, for example laterally as depicted in FIGS. 8A and 8B rather that vertically. The handle 106 of the probe 105 preferably has markings to indicate the rotational orientation of the outlets 124b.

FIG. 8A depicts the application of Rf energy in a monopolar manner between electrode emitter 128 and ground pad 170, which thus causes asymmetric heating wherein surface portion 180 heating results in greater polymerization therein. As can be seen in FIG. 8A, the volume of fill material thus exhibits a gradient in a flowability property, for example with surface region 180 having a higher viscosity than inflowing material 120' as it is ejected from outlet 124a. In one embodiment, the gradient is continuous. Such heating at the plume periphery 165 can create an altered, highly viscous surface region 180. This step of the method can transform the fill material to have a gradient in flowability in an interval of about 5 seconds to 500 seconds with surface portion 180 being either a highly viscous, flowable layer or an elastomer that is expandable. In preferred embodiments, the interval of energy delivery required less than about 120 seconds to alter fill material to a selected asymmetric condition. In another aspect of the invention, the Rf energy application for creating the gradient in flowability also can be optimized for coagulating and sealing adjacent tissue.

The combination of the viscous surface portion 180 and the tissue coagulum 172 may function as an in-situ created stretchable, but substantially flow-impervious, layer to contain subsequent high pressure inflows of fill material. Thus, the next step of the method of the invention is depicted in FIG. 8B which includes injecting additional fill material 120' under high pressure into the interior of the initial volume of fill material 120 that then has a highly viscous, expandable surface. The viscous, expandable surface desirably surrounds cancellous bone By this means, the subsequent injection of fill material can expand the fill volume to apply retraction forces on the vertebra endplates 166a and 166b to provide vertical jacking forces, distracting cortical bone, for restoring vertebral height, as indicated by the arrows in FIG. 8B. The system can generate forces capable of breaking callus in cortical bone about a vertebral compression fracture when the fracture is less than completely healed.

In one embodiment, the method includes applying Rf energy to create highly viscous regions in a volume of fill material and thereafter injecting additional fill material 120 to controllably expand the fill volume and control the direction of force application. The scope of the method further includes applying Rf energy in multiple intervals or contemporaneous with a continuous flow of fill material. The scope of the method also includes applying Rf in conjunction with imaging means to prevent unwanted flows of the fill material. The scope of the invention also includes applying Rf energy to polymerize and accelerate hardening of the entire fill volume after the desired amount of fill material has been injected into a bone.

Figure 9A:
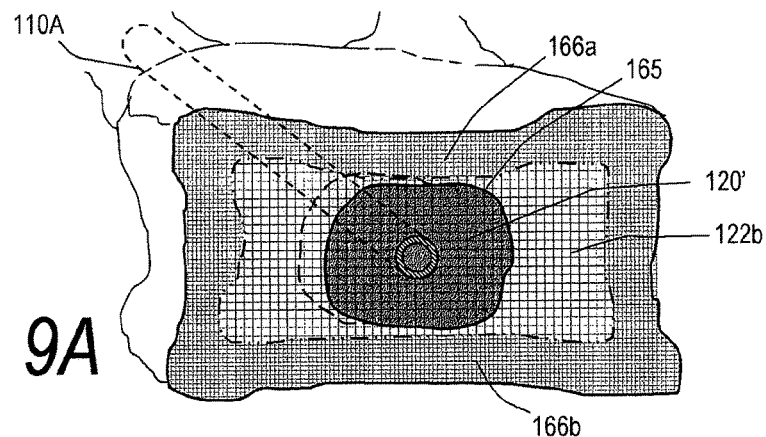
FIG. 9A is a schematic sectional view of one step in a method for treating bone, in accordance with one embodiment.
Figure 9B:
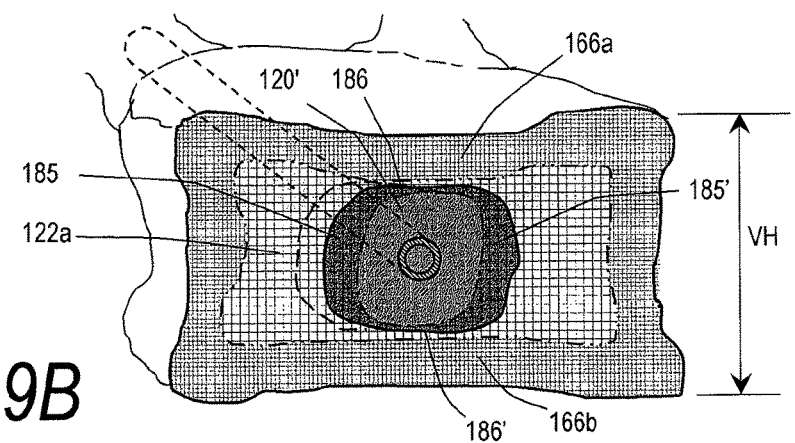
FIG. 9B is a schematic sectional view of another step in a method for treating bone, in accordance with one embodiment.
Figure 9C:
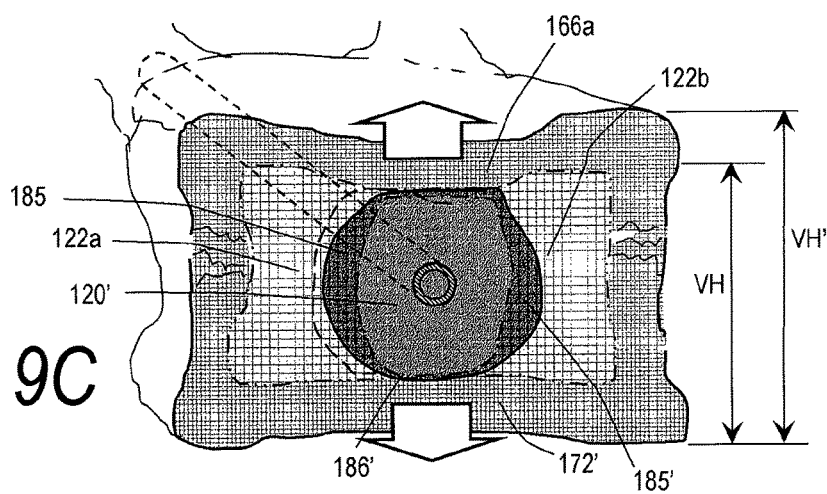
FIG. 9C is a schematic sectional view of still another step in a method for treating bone, in accordance with one embodiment.

In another embodiment, the method includes creating Rf current densities in selected portions of the volume of fill material 120 to create asymmetric fill properties based on particular characteristics of the vertebral body. For example, the impedance variances in cancellous bone and cortical bone can be used to create varied Rf energy densities in fill material 120 to create asymmetric properties therein. Continued injection of fill material 120 are thus induced to apply asymmetric retraction forces against cortical endplates 166a and 166b, wherein the flow direction is toward movement or deformation of the lower viscosity portions and away from the higher viscosity portions. In FIGS. 9A-9C, it can be seen that in a vertebroplasty, the application of Rf energy in a mono-polar manner as in FIG. 6 naturally and preferentially creates more highly viscous, deeper "altered" properties in surfaces of the lateral peripheral fill volumes indicated at 185 and 185' and less viscous, thinner altered surfaces in the superior and inferior regions 186 and 186' of fill material 120. This effect occurs since Rf current density is localized about paths of least resistance which are predominantly in locations proximate to highly conductive cancellous bone 122a and 122b. The Rf current density is less in locations proximate to less conductive cortical bone indicated at 166a and 166b. Thus, it can be seen in FIG. 9B that the lateral peripheral portions 185 and 185' of the first flows of fill material 120 are more viscous and resistant to flow and expansion than the thinner superior and inferior regions. In FIG. 9C, the asymmetrical properties of the initial flows of fill material 120 allows the continued flows to apply retraction forces in substantially vertical directions to reduce the vertebral fracture and increase vertebral height, for example from VH (FIG. 9B) to VH' in FIG. 9C.

Figure 10A:
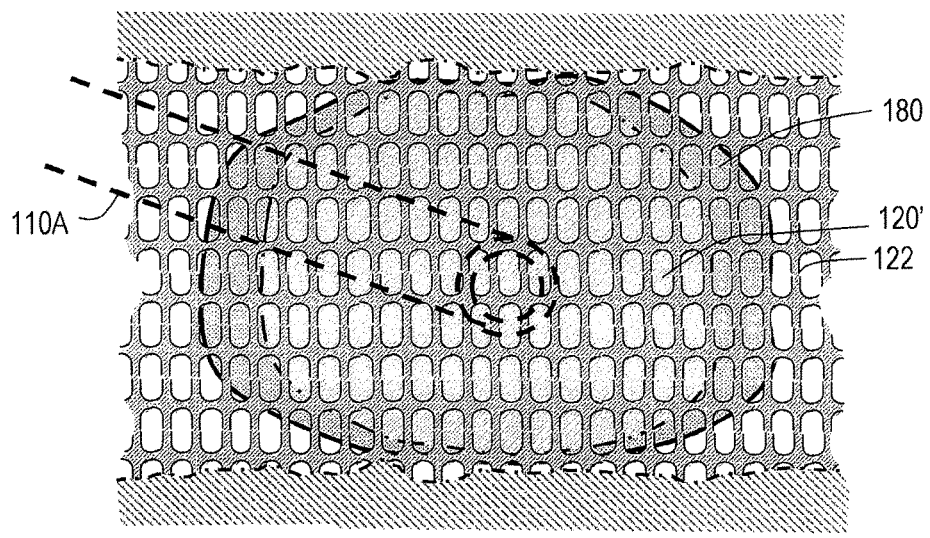
FIG. 10A is a schematic sectional view of a step in a method for treating bone, in accordance with another embodiment.
Figure 10B:
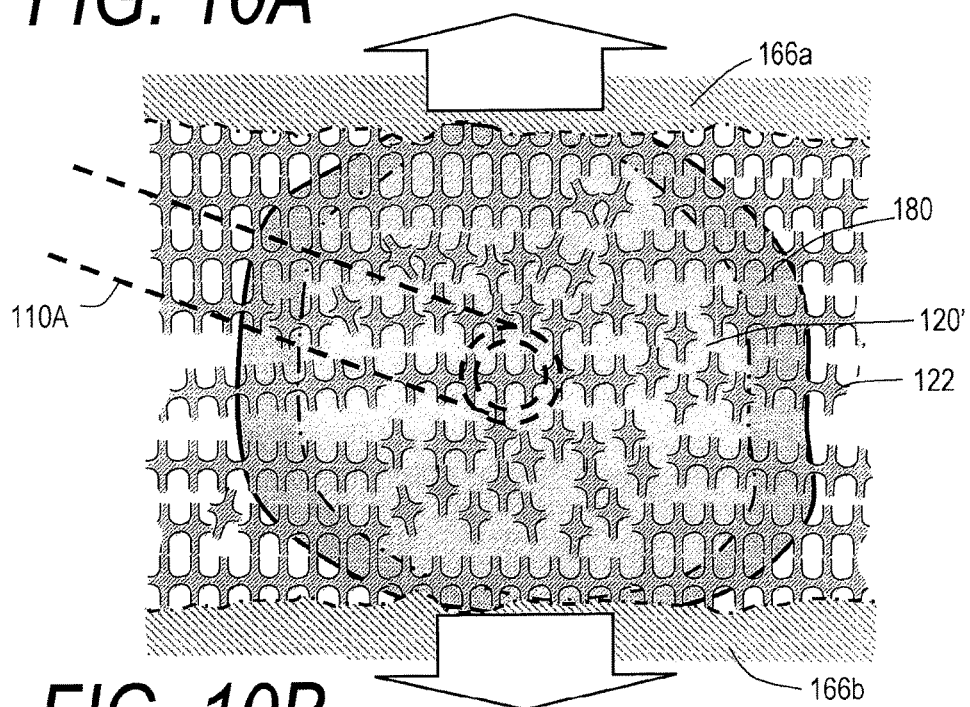
FIG. 10B is a schematic sectional view of another step in a method for treating bone, in accordance with another embodiment.

FIGS. 10A and 10B are schematic views that further depict a method corresponding to FIGS. 9B and 9C that comprises expanding cancellous bone for applying retraction forces against cortical bone, e.g., endplates of a vertebra in a vertebroplasty. As can be seen in FIG. 10A, an initial volume of flowable fill material 120 is injected into cancellous bone wherein surface region 180 is altered as described above to be highly viscous or to comprise and elastomer that is substantially impermeable to interior flows but still be expandable. The surface region 180 surrounds subsequent flows of fill material 120' which interdigitate with cancellous bone. Thereafter, as shown in FIG. 10B, continued high pressure inflow into the interior of the fill material thereby expands the cancellous bone 122 together with the interdigitated fill material 120'. As can be seen in FIG. 10B, the expansion of cancellous bone 122 and fill material 120' thus applies retraction forces to move cortical bone endplates 166a and 166b. The method of expanding cancellous bone can be used to reduce a bone fracture such as a vertebral compression fracture and can augment or restore the height of a fractured vertebra. The system thus can be used to support retract and support cortical bone, and cancellous bone. The method can also restore the shape of an abnormal vertebra, such as one damaged by a tumor.

After utilizing system 100 to introduce, alter and optionally harden fill material 120 as depicted in FIGS. 9A-9C and 10A-10B, the introducer 110A can be withdrawn from the bone. Alternatively, the introducer 110A can have a release or detachment structure indicated at 190 for de-mating the working end from the proximal introducer portion as described in U.S. patent application Ser. No. 11/130,843, filed May 16, 2005, the entirety of which is hereby incorporated by reference.

Figure 11A:
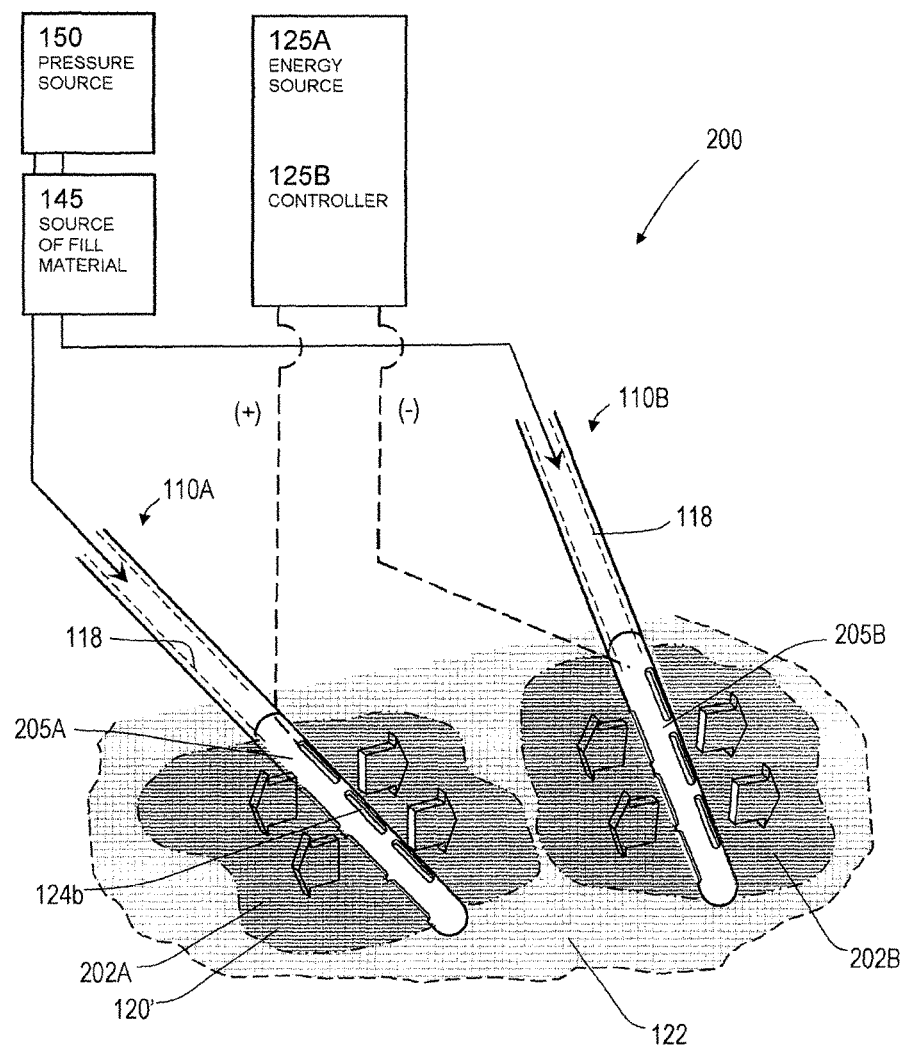
FIG. 11A is a schematic perspective view of a system for treating bone, in accordance with another embodiment.
Figure 11B:
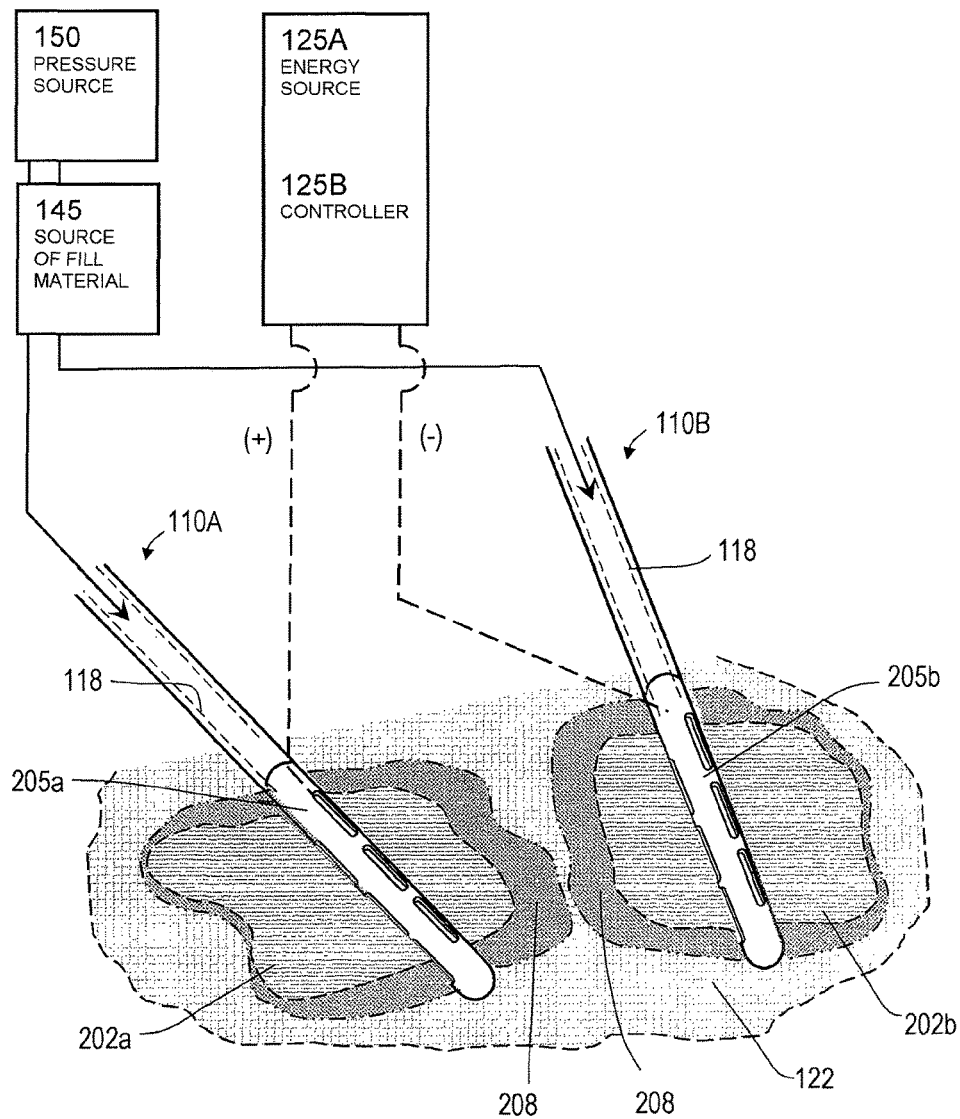
FIG. 11B is a schematic perspective view of the system in FIG. 11A, applying energy to a fill material.

Another system embodiment 200 for controlling flow directions and for creating asymmetric properties is shown in FIGS. 11A and 11B, wherein first and second introducers 110A and 110B similar to those described above are used to introduce first and second independent volumes 202a and 202b of fill material 120 in a bilateral approach. In this embodiment, the two fill volumes function as opposing polarity electrodes in contact with electrodes 205a and 205b of the working ends. Current flow between the electrodes thus operates in a bi-polar manner with the positive and negative polarities indicated by the (+) and (−) symbols. In this method, it also can be seen that the highest current density occurs in the three dimensional surfaces of volumes 202a and 202b that face one another. This results in creating the thickest, high viscosity surfaces 208 in the medial, anterior and posterior regions and the least "altered" surfaces in the laterally outward regions. This method is well suited for preventing posterior and anterior flows and directing retraction forces superiorly and inferiorly since lateral flow are contained by the cortical bone at lateral aspects of the vertebra. The system can further be adapted to switch ohmic heating effects between the bi-polar manner and the mono-polar manner described previously.

Figure 12:
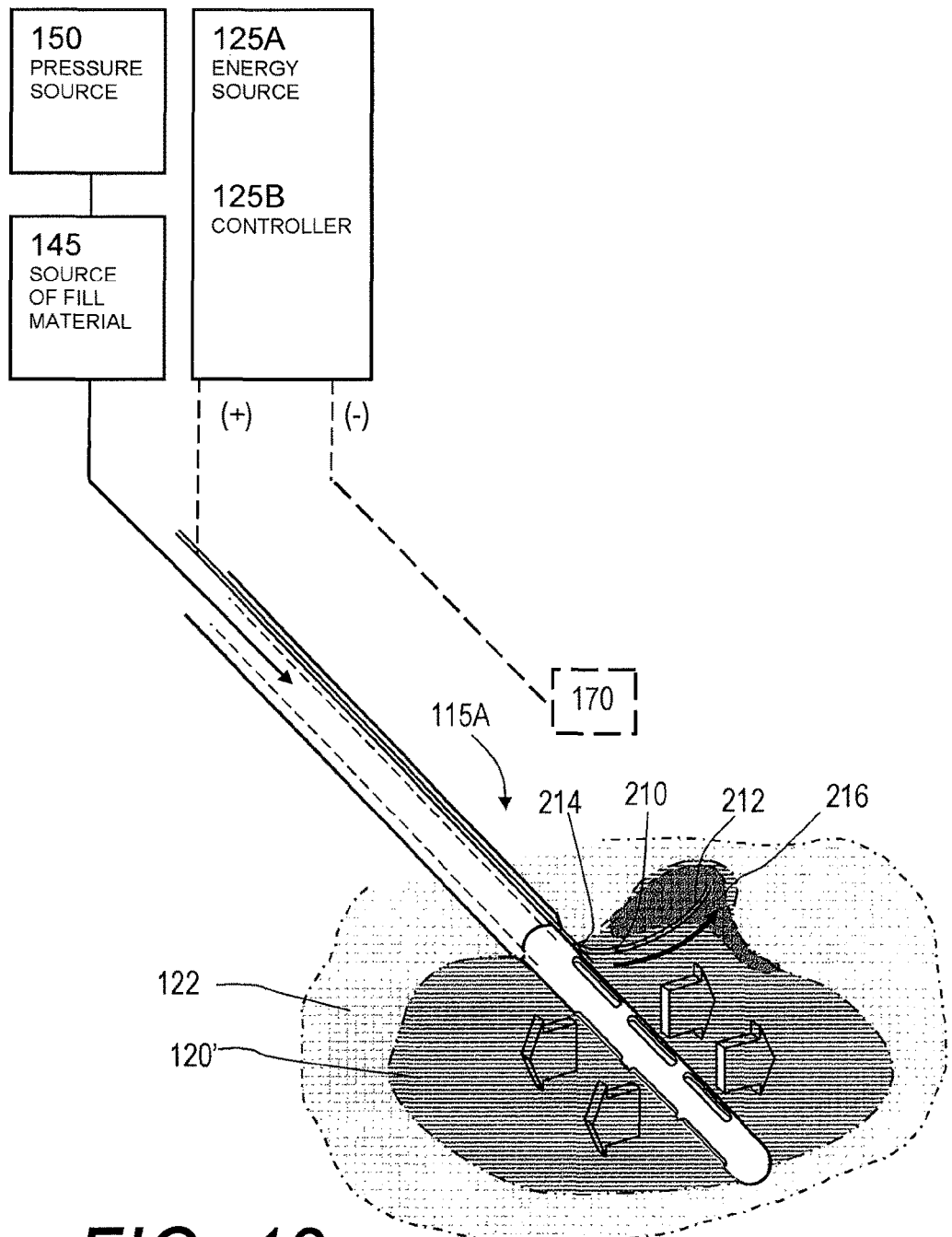
FIG. 12 is a schematic perspective view of a system for treating bone, in accordance with another embodiment.

Now referring to FIG. 12, another embodiment is shown wherein a translatable member 210 that functions as an electrode is carried by introducer 110A. In a preferred embodiment, the member 210 is a superelastic nickel titanium shape memory wire that has a curved memory shape. The member 210 can have a bare electrode tip 212 with a radiopaque marking and is otherwise covered by a thin insulator coating. In FIG. 12, it can be seen that the introducer can be rotated and the member can be advanced from a port 214 in the working end 115A under imaging. By moving the electrode tip 212 to a desired location and then actuating RF current, it is possible to create a local viscous or hardened region 216 of fill material 120. For example, if imaging indicates that fill material 120 is flowing in an undesired direction, then injection can be stopped and Rf energy can be applied to harden the selected location.

Figure 13:
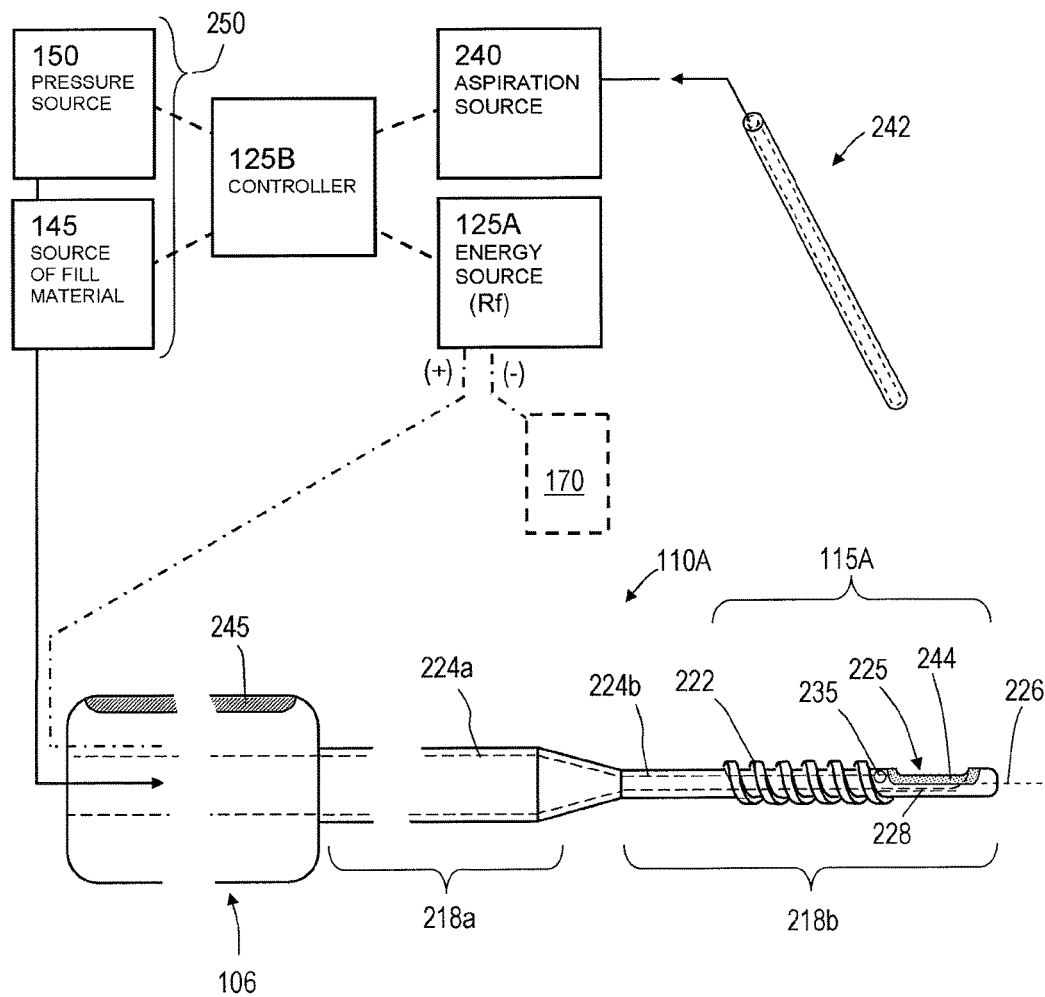
FIG. 13 is a schematic view of another embodiment of a bone cement delivery system together with an aspiration source a working end of an introducer, in accordance with one embodiment.

FIG. 13 illustrates another embodiment of the introducer 110A which includes a transition in cross-sectional dimension to allow for decreased pressure requirements for introducing bone cement through the length of the introducer. In the embodiment of FIG. 13, the proximal handle end 106 is coupled to introducer 110A that has a larger diameter proximal end portion 218a that transitions to a smaller diameter distal end portion 218b configured for insertion into a vertebral body. The distal end portion 218b includes exterior threads 222 for helical advancement and engagement in bone to prevent the introducer from moving proximally when cement is injected into a vertebral body or other bone, for example to augment vertebral height when treating a VCF. The bore that extends through the introducer 110A similarly transitions from larger diameter bore portion 224a to smaller diameter bore portion 224b. The embodiment of FIG. 13 utilizes a bore termination or slot 225 in a sidewall of the working end 115A for ejecting bone cement at a selected radial angle from the axis 226 of the introducer for directing cement outflows within a vertebral body.

Still referring to FIG. 13, the introducer 110A is coupled to bone cement source 145 and pressure source 150 as described previously that is controlled by controller 125B. Further, an energy source 125A (e.g., Rf source) is coupled to an energy delivery mechanism in the working end 115A for applying energy to a cement flow within bore 224b. In the embodiment of FIG. 13, the introducer can be fabricated of a strong reinforced plastic such a polymide composite with a sleeve electrode 228 in bore 224a and inward of the bore termination slot 225, similar to electrode 128 depicted in FIG. 3A. The electrode 228 in FIG. 13 is coupled to Rf source 125A for operating in a mono-polar manner in cooperation with a return ground pad indicated at 170. The controller 125B again is operatively connected to Rf source 125A to adjust energy delivery parameters in response to feedback from a thermocouple 235 in the bore 124a or in response to measuring impedance of the cement flow. In FIG. 13, the controller 125B further is operationally connected to an aspiration source 240 that is coupled to a needle-like introducer sleeve 242 that can be inserted into a bone to apply suction forces to the interior of vertebra for relieving pressure in the vertebra and/or extracting fluids, bone marrow and the like that could migrate into the venous system. The use of such an aspiration system will be described further below.

In FIG. 13, the introducer 110A has a larger diameter bore 224a that ranges from about 4 mm. to 10 mm. and preferably is in the range of about 5 mm to 6 mm. The smaller diameter bore 224b can range from about 1 mm. to 3 mm. and preferably is in the range of about 1.5 mm to 2.5 mm. The exterior threads 222 can be any suitable height with single or dual flights configured for gripping cancellous bone. The thread height and length of the reduced diameter section 218b are configured for insertion into a vertebra so that the port 225 can be anteriorly or centrally located in the vertebral body. The working end 115A further carries a radiopaque marking 244 for orienting the radial angle of the introducer and bore termination port 225. In FIG. 13, the radiopaque marking 244 is elongated and surrounds port 225 in the introducer sidewall. The handle 106 also carries a marking 245 for indicating the radial angle of port 225 to allow the physician to orient the port by observation of the handle.

Figure 14A:
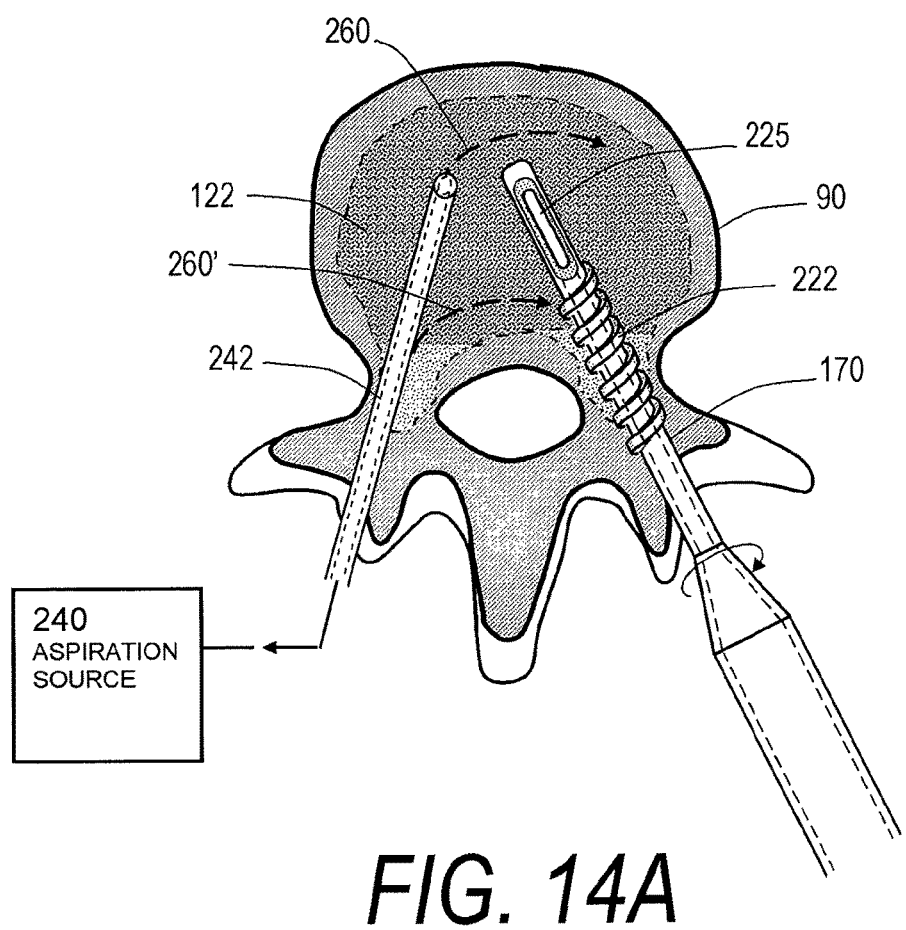
FIG. 14A is a sectional view of a working end of an introducer as in FIG. 13 showing the orientation of a cement injection port in a vertebra.
Figure 14B:
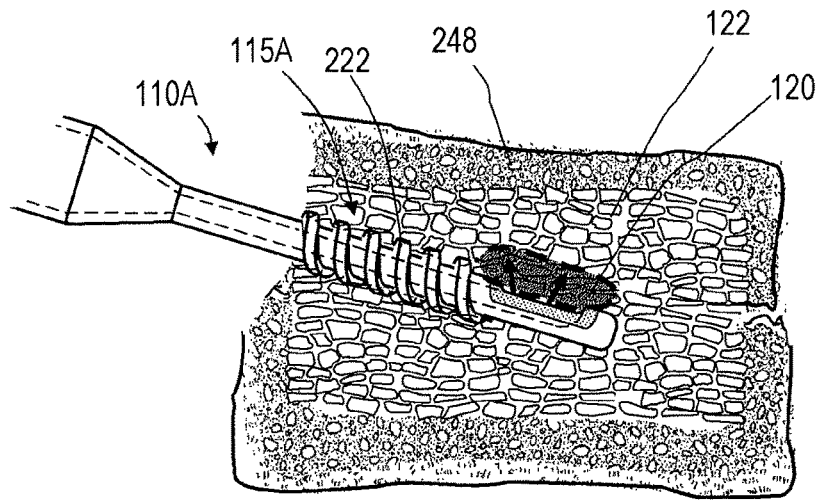
FIG. 14B is a sectional view of the working end of FIG. 14A showing an initial inflow of bone cement.
Figure 14C:
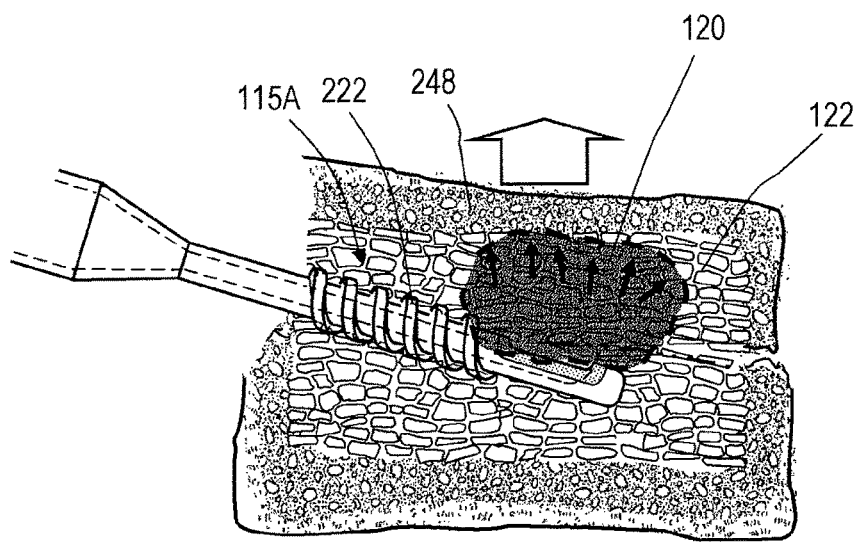
FIG. 14C is a sectional view of the working end of FIG. 14B showing an additional inflow of bone cement to reduces a vertebral fracture.

Now referring to FIGS. 14A-14C, the working end 115A of the introducer of FIG. 13 is shown after being introduced into cancellous bone 122 in vertebra 90. FIG. 14A illustrates a horizontal sectional view of vertebra 90 wherein the bore termination port 225 is oriented superiorly to direct cement inflows to apply forces against cancellous bone 122 and the superior cortical endplate 248 of the vertebra. A method of the invention comprises providing a flow source 250 (the pressure source 150 and cement source 145, in combination, are identified as flow source 250 in FIG. 13) for bone cement inflows and a controller 125B for control of the bone cement inflows, and inflowing the bone cement into a vertebral body wherein the controller adjusts an inflow parameter in response to a measured characteristic of the cement. In one method, the measured characteristic is temperature of the bone cement measured by thermocouple 235 in the working end 115A. The controller 125B can be any custom computerized controller. In one embodiment, the system can utilize a commercially available controller manufactured by EFD Inc., East Providence, R.I. 02914, USA for flow control, wherein either a positive displacement dispensing system or an air-powered dispensing system can coupled to the flow source 250. In response to feedback from thermocouple 235 that is read by the controller 125B, any inflow parameter of the bone cement flow can be adjusted, for example cement injection pressure, the inflow rate or velocity of the bone cement flows or the acceleration of a bone cement flow. The controller 125B also can vary any inflow parameter with time, for example, in pulsing cement inflows to thereby reduce a vertebral fracture, or move cancellous or cortical bone (see FIGS. 14A-14B). The cement 120 can be introduced in suitable volumes and geometries to treat fractures or to prophylactically treat a vertebra.

In another method corresponding to the invention, the flow source 250, controller 125B and Rf energy source 125A are provided as shown in FIG. 13. The controller 125B again is capable of adjusting any bone cement delivery parameter in response to impedance and/or temperature. The controller 125B adjusts at least one cement delivery parameter selected from cement volume, pressure, velocity and acceleration of the inflowing cement. The controller 125B also can vary pressure of the inflowing cement or pulse the cement inflows. In this embodiment, the controller 125B also is capable of adjusting energy delivered from Rf energy source 125A to the inflowing cement 120 in response to impedance, temperature, cement viscosity feedback or cement flow parameters to alter cement viscosity as described above. Cement viscosity can be calculated by the controller 125B from temperature and pressure signals. The controller 125B also is capable of being programmed with algorithms to ramp-up and ramp down power in one or more steps, or can be programmed to pulse power delivery to the bone cement 120 (FIGS. 14A-14BA).

As can be seen in FIGS. 14B and 14C, the inflowing cement 120 can be directed to apply forces against cancellous bone 122 and the superior cortical endplate 248 of the vertebra, or the working end can be rotated to introduce cement 120 and apply forces in other directions. In this embodiment, the extension of the working end 115A in cancellous bone serves as a support for causing expansion pressures to be directed substantially in the direction of cement flows. The method of treating the vertebra includes translating (by helical advancement) and rotating the introducer 110A to thereby alter the direction of cement introduction. In another embodiment (not shown), the introducer 110A can comprise an assembly of first and second concentric sleeves wherein the outer sleeve has threads 222 for locking the assembly in bone and the inner sleeve is rotatable to adjust the angular direction of port 225 wherein the sleeves are locked together axially. This embodiment can be used to intermittently angularly adjust the direction of cement outflows while helical movement of the outer sleeve adjusts the axial location of port 225 and the cement outflows.

In another method of the invention, referring back to FIG. 14A, the aspiration introducer sleeve 242 can be inserted into the vertebral body, for example through the opposing pedicle. The controller 125B can be programmed to alter aspiration parameters in coordination with any bone cement inflow parameter. For example, the cement inflows can be pulsed and the aspiration forces can be pulsed cooperatively to extract fluids and potentially embolic materials, with the pulses synchronized. In one method, the cement inflows are pulsed at frequency ranging between about 1 per second and 500 per second with an intense, high acceleration pulse which causes bone marrow, fat, blood and similar materials to become susceptible to movement while at the same time the aspiration pulses are strong to extract some mobile marrow etc into the aspiration sleeve 242. In FIG. 14A, the aspiration sleeve 242 is shown with single port in it distal end. It should be appreciated that the scope of the invention and its method of use includes an aspiration sleeve 242 that has a plurality of inflow ports along the length of the sleeve and the sleeve also can be curved or can be of a shape memory alloy (e.g., Nitinol) to for introduction in a curved path in the anterior of posterior region of a vertebral body as indicated by lines 260 and 260' in FIG. 14A. In another embodiment, the aspiration sleeve 242 can extend through the introducer 110A or can comprise an outer concentric sleeve around the introducer 110A.

Figure 15A:
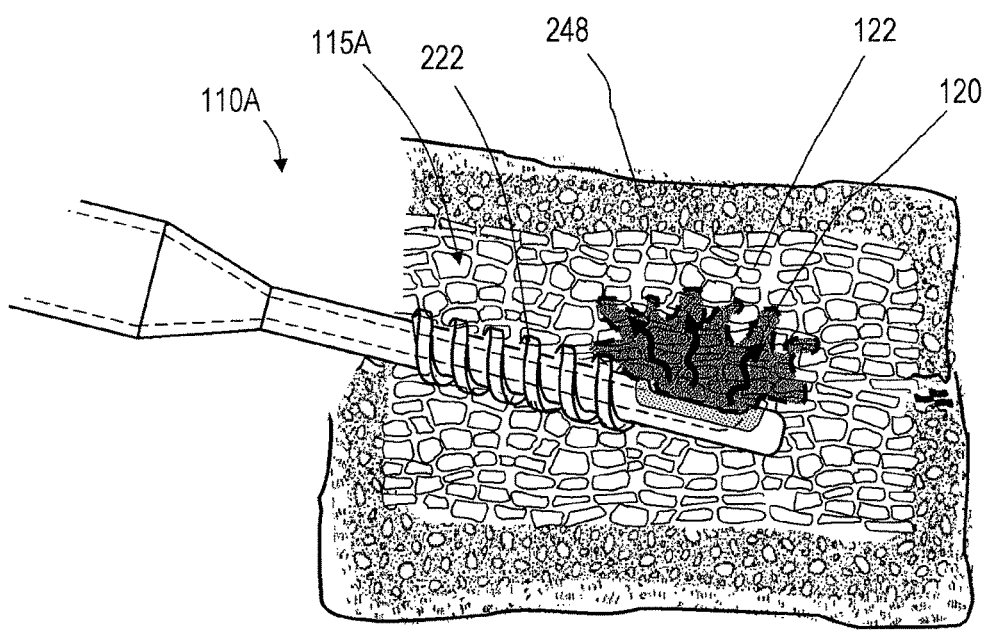
FIG. 15A is a sectional view of a vertebra depicting a first mode of operation wherein an initial flow of bone cement is provided under selected flow parameters that allow cement interdigitation into cancellous bone.
Figure 15B:
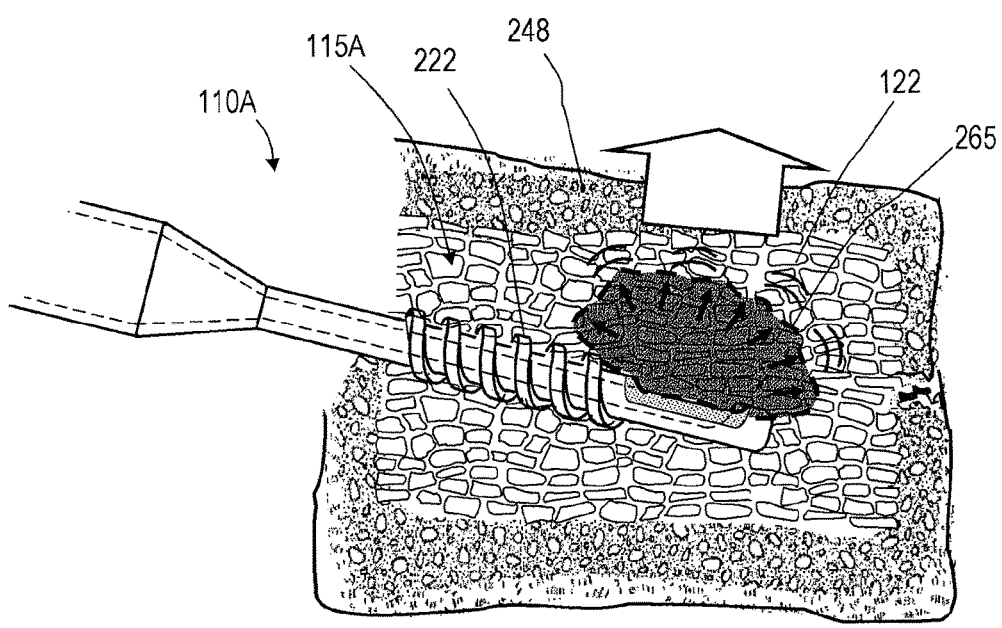
FIG. 15B is a sectional view of a vertebra similar to FIG. 15A depicting a second mode of operation wherein cement flows are provided in a high acceleration pulse that disallows cement interdigitation into cancellous bone.

FIGS. 15A and 15B illustrates another method corresponding to the invention wherein the controller 125B and pressure source 150 are configured to introduce a flowable cement into the interior of a vertebra one under widely varying velocities and rates of acceleration to optionally (i) provide first slow flow rates to allow cement flow and interdigitition into and through cancellous bone, and (ii) provide second higher flow rates that disallow cement interdigitition and flow into and through cancellous bone. At suitable high acceleration and flow velocity, for example in a pulse of cement flow into bone, the accelerated flow apply forces to bone substantially across the surface of the cement plume which can displace cancellous bone rather than allowing the cement to flow into the cancellous bone. FIG. 14A illustrates the system of FIG. 13 in a method of use wherein the controller 125B and pressure source 150 are actuated to cause a volume of cement 120 to flow into cancellous bone 122 under a suitable low pressure to allow the cement to interdigitate with, and flow into, the cancellous bone. The flow of cement depicted in FIG. 14A can be accompanied by the application of aspiration forces as described above. FIG. 15B illustrates another aspect of the method wherein the controller 125B and pressure source 150 are actuated to flow cement with a high acceleration rate and velocity that disallows the cement from having time to flow into pores of the cancellous bone. The acceleration and velocity are selected to disallow cement interdigitation which thereby causes the application of force to bone across the surface of the cement plume 265 (FIG. 15B). The application of such forces across the surface of cement plume 265 is further enabled by providing a suitable high viscosity cement as described above, which includes selectively increasing cement viscosity by means of energy delivery thereto. The method of the invention can include one or more sequences of flowing cement into the bone to first cause cement interdigitation (FIG. 15A) and then to apply expansion forces to the bone by at least one high acceleration flow (FIG. 15B). Of particular interest, the method of using high acceleration flows, for example in pulses, causes the cement volume to apply forces to bone akin to the manner is which a mechanical expander or balloon expander would apply forces to bone. That is, expansion forces are applied across the entire surface of cement plume 265 similar to then manner in which mechanical instruments apply expanding forces across the bone engaging surface of the instrument. The methods are adapted for reducing a vertebral fracture and for selectively applying forces to move cancellous bone and cortical bone.

The scope of the invention further extends to cure-on-demand fill materials that can be used for disc nucleus implants, wherein the conductive fill material is injected to conform to the shape of a space and wherein Rf current is then applied to increase the modulus of the material on demand to a desired level that is adapted for dynamic stabilization. Thus, the Rf conductive fill material 120 can be engineered to reach a desired modulus that is less than that of a hardened fill material used for bone support. In this embodiment, the fill material is used to support a disc or portion thereof. The cure-on-demand fill material also can be configured as an injectable material to repair or patch a disc annulus as when a tear or herniation occurs.

The scope of the invention further extends to cure-on-demand fill material that can be used for injection into a space between vertebrae for intervertebral fusion. The injection of fill material can conform to a space created between two adjacent vertebrae, or can be injected into notches or bores in two adjacent vertebrae and the intervening space, and then cured by application of Rf current to provide a substantially high modulus block to cause bone fusion.

In any embodiment such as for intervertebral fusion or for bone support in VCFs, the system can further include the injection of a gas (such as carbon dioxide) into the fill material before it is injected from a high pressure source. Thereafter, the gas can expand to form voids in the fill material as it is cured to create porosities in the hardened fill material for allowing rapid bone ingrowth into the fill material.

In related methods of the invention, the system of the invention can use any suitable energy source, other that radiofrequency energy, to accomplish the purpose of altering the viscosity of the fill material 120. The method of altering fill material can be at least one of a radiofrequency source, a laser source, a microwave source, a magnetic source and an ultrasound source. Each of these energy sources can be configured to preferentially deliver energy to a cooperating, energy sensitive filler component carried by the fill material. For example, such filler can be suitable chromophores for cooperating with a light source, ferromagnetic materials for cooperating with magnetic inductive heating means, or fluids that thermally respond to microwave energy.

The scope of the invention includes using additional filler materials such as porous scaffold elements and materials for allowing or accelerating bone ingrowth. In any embodiment, the filler material can comprise reticulated or porous elements of the types disclosed in U.S. patent application Ser. No. 11/146,891, filed Jun. 7, 2005, titled "Implants and Methods for Treating Bone" which is incorporated herein by reference in its entirety and should be considered a part of this specification. Such fillers also can carry bioactive agents. Additional fillers, or the conductive filler, also can include thermally insulative solid or hollow microspheres of a glass or other material for reducing heat transfer to bone from the exothermic reaction in a typical bone cement component.

The above description of the invention is intended to be illustrative and not exhaustive. Particular characteristics, features, dimensions and the like that are presented in dependent claims can be combined and fall within the scope of the invention. The invention also encompasses embodiments as if dependent claims were alternatively written in a multiple dependent claim format with reference to other independent claims. Specific characteristics and features of the invention and its method are described in relation to some figures and not in others, and this is for convenience only. While the principles of the invention have been made clear in the exemplary descriptions and combinations, it will be obvious to those skilled in the art that modifications may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

Of course, the foregoing description is that of certain features, aspects and advantages of the present invention, to which various changes and modifications can be made without departing from the spirit and scope of the present invention. Moreover, the bone treatment systems and methods need not feature all of the objects, advantages, features and aspects discussed above. Thus, for example, those skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed bone treatment systems and methods.

What is claimed is:

1. A system for treating bone, comprising:
a bone cement injection assembly having a flow channel extending therethrough for injecting bone cement into an interior of a bone;
a thermal energy emitter coupleable to an energy source and configured to deliver energy to the bone cement as it flows through the flow channel to controllably alter the viscosity of the bone cement within the flow channel; and
a controller coupleable to the energy source, the controller comprising algorithms for adjusting power delivery applied by the energy source, wherein the controller includes algorithms for adjusting power delivery based on at least one of the following: impedance of the bone cement within the flow channel, temperature of the bone cement within the flow channel, volume of the bone cement within the flow channel, or flow rate of the bone cement within the flow channel.

2. The system of claim 1, wherein the energy source is at least one of a radiofrequency source, a resistive heat source, a laser source, a microwave source, a magnetic source, or an ultrasound source.

3. The system of claim 2, wherein the energy source is a radiofrequency source.

4. The system of claim 1, wherein the controller includes algorithms for adjusting power delivery based on impedance of the bone cement within the flow channel.

5. The system of claim 1, wherein the controller includes algorithms for adjusting power delivery based on temperature of the bone cement within the flow channel.

6. The system of claim 1, wherein the controller includes algorithms for adjusting power delivery based on flow rate of the bone cement within the flow channel.

7. The system of claim 1, wherein the controller includes algorithms for adjusting power delivery based on volume of the bone cement within the flow channel.

8. The system of claim 1, wherein the controller is configured to adjust power delivery applied by the energy source to alter the bone cement to a viscosity that is sufficient to controllably permeate and interdigitate with cancellous bone.

9. The system of claim 1, further comprising:
a source of bone cement operatively coupleable to the flow channel.

10. The system of claim 9, wherein the controller is configured to vary the volume of bone cement introduced into the flow channel.

11. The system of claim 1, wherein the thermal energy emitter is disposed about a distal termination of the flow channel.

12. The system of claim 1, wherein the thermal energy emitter comprises one or more electrodes.

13. The system of claim 1, wherein the bone cement injection assembly comprises a thermally insulative interior sleeve that defines at least a portion of the flow channel.

14. A system for treating bone, comprising:
a bone cement injection assembly having a flow channel extending therethrough for injecting bone cement into an interior of a bone;
a thermal energy emitter coupleable to an energy source and configured to deliver energy to the bone cement as it flows through the flow channel to controllably alter the viscosity of the bone cement within the flow channel; and
a controller coupleable to the energy source, the controller comprising algorithms for adjusting power delivery applied by the energy source, wherein the controller is configured to adjust power delivery applied by the energy source to alter the bone cement to a viscosity that is sufficient to controllably permeate and interdigitate with cancellous bone.

15. The system of claim 14, wherein the energy source is at least one of a radiofrequency source, a resistive heat source, a laser source, a microwave source, a magnetic source, or an ultrasound source.

16. The system of claim 15, wherein the energy source is a radiofrequency source.

17. The system of claim 14, further comprising:
a source of bone cement operatively coupleable to the flow channel.

18. The system of claim 17, wherein the controller is configured to vary the volume of bone cement introduced into the flow channel.

19. A system for treating bone, comprising:
a bone cement injection assembly having a flow channel extending therethrough for injecting bone cement into an interior of a bone;
a source of bone cement operatively coupleable to the flow channel;
a thermal energy emitter coupleable to an energy source and configured to deliver energy to the bone cement as it flows through the flow channel to controllably alter the viscosity of the bone cement within the flow channel, wherein the energy source is at least one of a radiofrequency source, a resistive heat source, a laser source, a microwave source, a magnetic source, or an ultrasound source; and
a controller coupleable to the energy source, the controller comprising algorithms for adjusting power delivery applied by the energy source.

20. The system of claim 19, wherein the energy source is a radiofrequency source.

* * * * *